(12) United States Patent
Kimmich et al.

(10) Patent No.: US 8,536,367 B2
(45) Date of Patent: *Sep. 17, 2013

(54) VINYL ESTER PRODUCTION FROM ACETYLENE AND CARBOXYLIC ACID UTILIZING HOMOGENEOUS CATALYST

(75) Inventors: Barbara F. M. Kimmich, Bernardsville, NJ (US); Hannah E. Toomey, Houston, TX (US); Qiang Yao, Baton Rouge, LA (US); G. Paull Torrence, League City, TX (US); Jan Cornelis van der Waal, Delft (NL); Michael J. Doyle, Amsterdam (NL)

(73) Assignee: Celanese International Corp., Irving, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/454,376

(22) Filed: Apr. 24, 2012

(65) Prior Publication Data

US 2012/0203025 A1    Aug. 9, 2012

Related U.S. Application Data

(63) Continuation of application No. 12/387,740, filed on May 7, 2009, now Pat. No. 8,173,830.

(51) Int. Cl.
*C07C 69/00* (2006.01)

(52) U.S. Cl.
USPC .......................................................... 560/129

(58) Field of Classification Search
None
See application file for complete search history.

(56) References Cited

U.S. PATENT DOCUMENTS 5,395,960 A * 3/1995 Heider et al. ................. 560/242
6,891,052 B1 * 5/2005 Tanner et al. ................. 554/161

* cited by examiner

*Primary Examiner* — Karl J Puttlitz
(74) *Attorney, Agent, or Firm* — Michael W. Ferrell

(57) ABSTRACT

A process for the selective production of vinyl ester by the reaction of a carboxylic acid with acetylene with a homogeneous catalyst is disclosed and claimed. In one aspect, esters of neoacids are provided.

18 Claims, 3 Drawing Sheets

VINYL ESTER PRODUCTION FROM ACETYLENE AND CARBOXYLIC ACID UTILIZING HOMOGENEOUS CATALYST

CLAIM FOR PRIORITY

This application is a continuation of U.S. patent application Ser. No. 12/387,740, filed on May 7, 2009, entitled "Vinyl Ester Production From Acetylene And Carboxylic Acid Utilizing Homogeneous Catalyst", now U.S. Pat. No. 8,173,830. The priority of U.S. patent application Ser. No. 12/387,740 is hereby claimed and its disclosure incorporated herein by reference in its entirety.

FIELD OF THE INVENTION

The present invention relates generally to a process for the production of vinyl ester from a carboxylic acid and acetylene. Specifically, the present invention relates to a series of homogeneous catalyst systems that are suitable for the production of vinyl ester from a reaction of acetylene with a variety of carboxylic acids. In preferred embodiments, the present invention relates to formation of vinyl benzoate (VB), vinyl 2-ethyl hexanoate (V2EH), and vinyl esters of various other neo carboxylic acids using homogeneous catalysts.

BACKGROUND

There is a long felt need for an economically viable process for the formation of vinyl carboxylates such as, for example, vinyl benzoate. Vinyl carboxylates, such as for example vinyl benzoate, find use in a variety of applications including, for example, paints, adhesives and various other coating formulations as well as cement mortar admixtures.

It is known in the art that vinyl esters can be formed from the reaction of corresponding carboxylic acid with acetylene. A variety of catalysts have been proposed including base metals such as zinc, cadmium and mercury as well as precious metal catalysts such as rhenium, ruthenium, palladium, etc. In fact, the zinc carboxylate catalyzed process has been commercialized by Hexion Specialty Chemicals for the production of VEOVA™ Monomer 10, which is a vinyl ester of VERSATIC™ Acid 10, a synthetic saturated monocarboxylic acid of highly branched structure containing ten carbon atoms. More particularly, see U.S Pat. No. 6,891,052 to Tanner et al., wherein is disclosed zinc carboxylate catalyst is used for the formation of vinyl ester from the reaction of carboxylic acid with acetylene.

Similarly, various other processes have been reported in the literature wherein a carboxylic acid is reacted with acetylene to form the corresponding vinyl ester. See U.S. Pat. No. 3,607,915 to Borsboom et al. and Transition-Metal-Catalyzed Addition of Heteroatom-Hydrogen Bonds to Alkynes, Alonso et al., Chem. Rev., 2004, 104 (6), 3079-3160. In particular, Borsboom et al. disclose generally another method involving zinc-catalyzed carboxylic acid reaction with acetylene, as already noted above. Whereas, Alonso et al. provide an analysis of the state of the art for catalytic addition chemistry of the reaction of acetylene with a carboxylic acid. See also, U.S. Pat. No. 2,066,075 to Reppe, German Patent No. DE 740678 to I.G. Farbenindustrie AG, U.S. Pat. Nos. 2,339,066 and 2,342,463 to Fischer et al., British Patent No. GB 641,438A to General Aniline and Film Corporation, U.S. Pat. No. 2,472,086 to Beller et al., Swiss Patent No. CH 324667 to Staeger Reinhard, U.S. Pat. No. 3,062,863 to Fernholz et al., U.S. Pat. No. 3,125,593 to Hargrave et al., U.S. Pat. No. 3,285,941 to Engel et al., German Patent No. DE 1237557 to Shell Internationale Research, U.S. Pat. No. 3,646,077 to Hübner et al., and U.S. Pat. No. 6,500,979 to Wiese et al.

It has also been reported in the literature that a variety of Group VIII metal complex catalysts are effective in the formation of vinyl esters by the reaction of carboxylic acids with acetylene. See, for example, U.S. Pat. No. 3,479,392 to Stern et al. and U.S. Pat. No. 5,395,960 to Heider et al. Both Stern et al. and Heider et al. disclose vinylation of aromatic carboxylic acids in the presence of a catalyst based on ruthenium, rhodium, palladium, osmium, iridium, or platinum. Stern et al. is specifically drawn to a process for producing substituted olefins from a reactant other than acetylene or acetylenic compounds, and Heider et al. only disclose branched aliphatic carboxylic acids suitable for the catalyzed vinylation reaction, providing examples including 2-ethyl-hexanoic acid, 4-tert-butylbenzoic acid, suberic acid, and monomethyl succinate. However, Heider et al. disclose use of only ruthenium metal as a catalyst by way of examples and employ a very low molar ratio of carboxylic acid to ruthenium of about 25 to 100. That is, Heider et al. conditions require a large amount of catalyst per mole of vinyl ester produced. Additionally, Heider et al. employ longer reaction times of 7 to 17 hours rendering these conditions unsuitable for an industrial operation.

Palladium used as a co-catalyst with a cadmium or zinc catalyst is also known in the vinylation art. See, for example, German Patent No. DE 1161878 to Farbwerke Hoechst Aktiengesellschaft and British Patent No. GB 1,130,245 to Shell Internationale Research. Both patents disclose vinylation of benzoic acid and acetylene in the presence of a zinc or cadmium catalyst and a palladium co-catalyst. The palladium compounds taught are, however, free palladium metal or palladium chloride, and the processes are typically operated at temperatures above 120° C.

U.S. Pat. No. 5,430,179 to Lincoln et al. describes a homogeneous process for vinyl ester synthesis, such as vinyl benzoate, by ruthenium-catalyzed addition of carboxylic acids, including benzoic acid, to alkynes, including acetylene. Lincoln et al. disclose reaction conditions that include an optional solvent, such as toluene or mineral oil, and a temperature range of from about 40 to about 200° C. Lincoln et al. further disclose use of a ruthenium catalyst selected from a group that includes ruthenium dodecacarbonyl in concentrations ranging from about 50,000 ppm to about 0.5 ppm ruthenium based on the weight of the liquid phase reaction medium optionally in combination with a ligand such as triphenyl phosphine, tris(methoxyphenyl)-phosphine, or tris(p-fluoromethylphenyl)phosphine. However, Lincoln et al., disclose only one example of forming vinyl pivalate from the reaction of pivalic acid with acetylene in the presence of ruthenium dicarbonyl acetate under the reaction conditions disclosed therein.

WO 2007/060176 A1 to BASF Aktiengesellschaft provides a process for preparing vinyl carboxylates by reacting a carboxylic acid with an alkyne compound in the presence of a catalyst selected from a group of metal compounds including rhenium-based compounds. BASF specifically discloses reacting benzoic acid and acetylene in the presence of dirheniumdecacarbonyl; see Example 1. The Example teaches a molar ratio of carboxyl group to rhenium atom of 388, wherein the reaction takes place in a toluene solvent at 140° C. over a reaction time of 6 hours. The reported yield is 99%.

However, it has now been found that none of the existing processes is suitable for the production of vinyl benzoate (VB) or vinyl 2-ethyl hexanoate (V2EH) via the vinylation reaction, particularly, the conventional zinc catalysts provided unacceptable reaction rates and yields for an industrial scale-up operation. The other methods as described hereinabove are equally not suitable for the production of vinyl esters such as VB or V2EH in an industrial scale. Thus it is desirable to develop economically viable catalytically active reactions to form vinyl esters, such as VB or V2EH from their respective carboxylic acids under mild reaction conditions.

SUMMARY OF THE INVENTION

It has now been unexpectedly found that vinyl esters such as vinyl benzoate can be made on an industrial scale from the reaction of a carboxylic acid with acetylene with high selectivity and yield. More particularly, this invention provides a homogeneous process for the selective formation of vinyl ester from a corresponding carboxylic acid and acetylene comprising: reacting a carboxylic acid, optionally dissolved in a suitable organic solvent, with acetylene in the presence of a catalyst at a suitable reaction temperature and pressure, and optionally in the presence of one or more ligands or additives or a mixture thereof The catalyst employed in the process of this invention is a metal complex. Examples of metal complexes that are suitable in this process of the invention include without any limitation iridium, palladium, platinum, rhenium, rhodium and ruthenium.

It has now been found that the use of certain ligands and additives enhance the catalytic activity of the catalysts of this invention. Various ligands and additives that can bring about the vinylation reaction with a carboxylic acid and acetylene can be employed in the process of this invention.

It has also been found that by suitable selection of the catalyst and optionally the ligand(s) and additive(s) and utilizing them in suitable amounts results in at least 50 percent (%) conversion of carboxylic acid and the selectivity to vinyl ester can be at least 50 percent (%). In addition, by suitable practice of this invention it is possible to attain a Relative Activity of at least 80 and up to about 2000.

Other aspects and advantages of the present invention are described in the detailed description below and in the claims.

BRIEF DESCRIPTION OF THE DRAWINGS:

The invention is described in detail below with reference to the appended drawings, wherein like numerals designate similar parts. In the Figures.

DETAILED DESCRIPTION OF THE INVENTION

Figure 1:
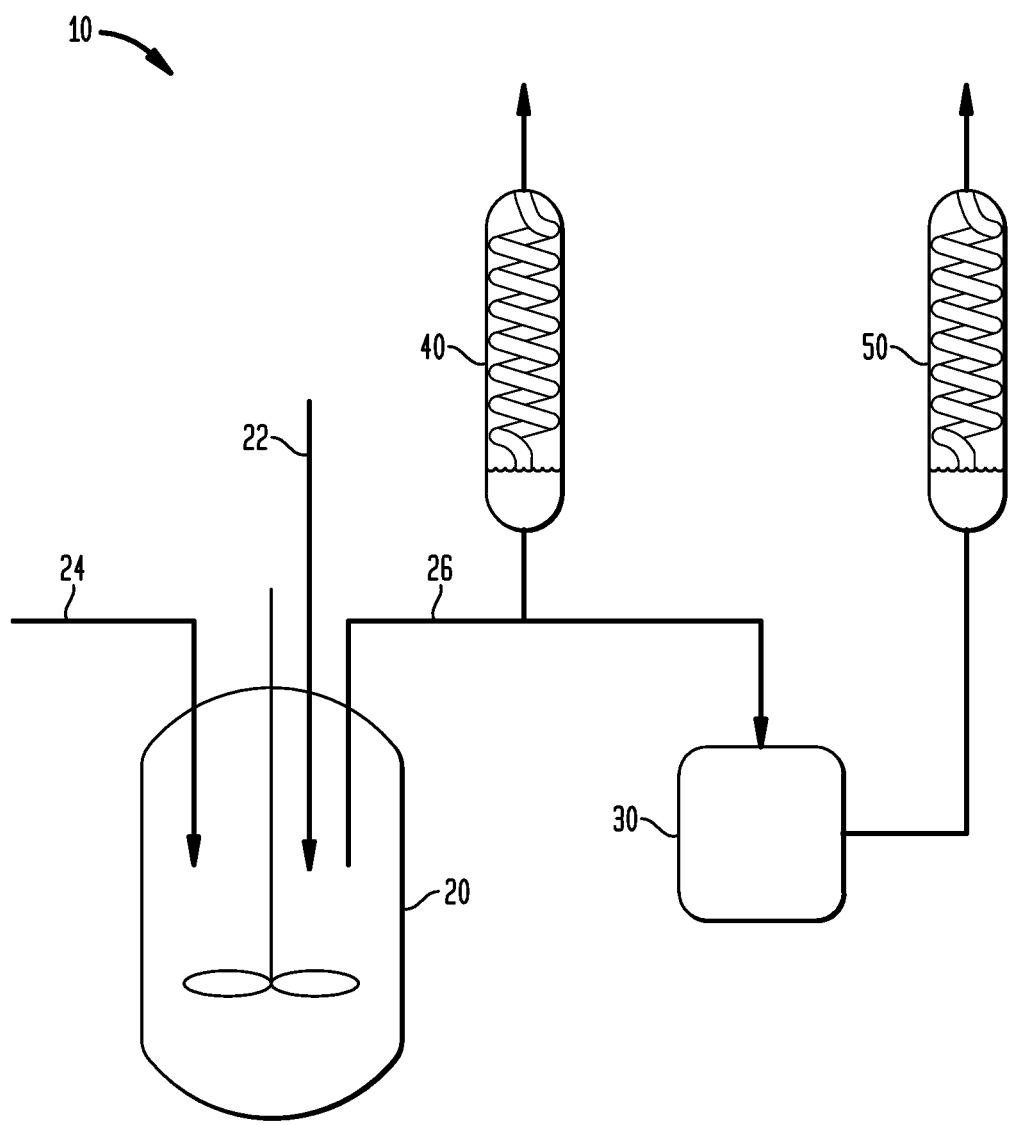
FIG. 1 is a schematic diagram of an apparatus suitable for producing vinyl ester from a carboxylic acid and acetylene in accordance with the process of the present invention.

The invention is described in detail below with reference to several embodiments and numerous examples. Such discussion is for purposes of illustration only. Modifications to particular examples within the spirit and scope of the present invention, set forth in the appended claims, will be readily apparent to one of skill in the art. Terminology used herein is given its ordinary meaning consistent with the exemplary definitions set forth immediately below.

As used herein, a homogeneous catalyst refers to a catalyst that is present in the same phase (e.g., liquid or gas) as the reactants during catalysis. In contrast, as used herein, a heterogeneous catalyst refers to a catalyst that is in a different phase than the reactants during catalysis.

As used herein, mole percent (mole % or %) and like terms refer to mole percent unless otherwise indicated. Weight percent (wt %) and like terms refer to weight percent unless otherwise indicated.

"Conversion" refers to the fraction of reactant consumed in the reaction and is expressed as a mass percentage based on the amount of carboxylic acid in the feed. The conversion of carboxylic acid (CA) is calculated from gas chromatography (GC) data using the following equation:

$$CA \text{ conversion } (\%) = 100 * \frac{\text{mass } CA, \text{in} - \text{mass } CA, \text{out}(GC)}{\text{mass } CA, \text{in}}$$

a where mass CA, in=mass of carboxylic acid loaded (weighed in) into the reactor, and mass CA, out (GC)=mass of carboxylic acid after the reaction based on GC data.

"Selectivity" refers to the amount of vinyl ester produced relative to the carboxylic acid consumed and is expressed as a mole percent based on converted carboxylic acid. For example, if the conversion is 50 mole % and 50 mole % of the converted carboxylic acid is converted to vinyl ester, we refer to the vinyl ester selectivity as 50%. Selectivity to vinyl ester (VE) is calculated from gas chromatography (GC) data using the following equation:

$$\text{Selectivity to } VE \text{ } (\%) = 100 * \frac{\text{mol } VE, \text{out } (GC)}{\text{mol } CA, \text{in} - \text{mol } CA, \text{out}(GC)}$$

"Yield" refers to the amount of vinyl ester produced relative to the carboxylic acid loaded into the reactor and is expressed as a mole percent based on carboxylic acid loaded into the reactor. Yield of vinyl ester (VE) is calculated from gas chromatography (GC) data using the following equation:

$$\text{Yield of } VE \text{ } (\%) = 100 * \frac{\text{mol } VE, \text{out } (GC)}{\text{mol } CA, \text{in } (GC)}$$

where mol CA, in=number of moles of carboxylic acid loaded (weighed in) into the reactor, mol CA, out (GC)=number of moles of carboxylic acid after the reaction based on GC data, and mol VE, out (GC)=number of moles of vinyl ester after the reaction based on GC data.

The catalyst activity is determined by Turnover Number (TON) using the following equation. TON refers to the average amount of desired product produced by each metal atom contained in the catalyst.

$$TON = \frac{\text{mol } VE, \text{out } (GC)}{\text{mol } Cat * N \text{ Metal atoms}}$$

where mol Cat=number of moles of catalyst loaded (weighed in) into the reactor, and N Metal atoms=number of metal atoms in the catalyst.

For Turnover Numbers determined under the following conditions, the

Turnover Number is referred to herein as Relative Activity. The conditions for determining Relative Activity of the catalyst system include a batch run duration of 4 hours, a charged molar ratio of carboxylic acid to catalyst metal of about 385:1, and a temperature of 120° C. When a ligand is used, the ligand is available in a molar ratio of ligand to catalyst metal of 1:1.

The reaction proceeds in accordance with the following chemical equation:

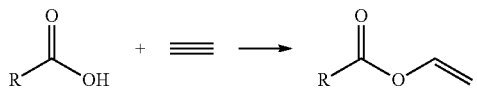

where R is an alkyl group, including a primary, a secondary or a tertiary alkyl group; a cycloalkyl group; or an aryl group such as phenyl. Thus, when R is phenyl, the acid employed is benzoic acid (BA) and the product formed is vinyl benzoate (VB) in accordance with the following chemical equation.

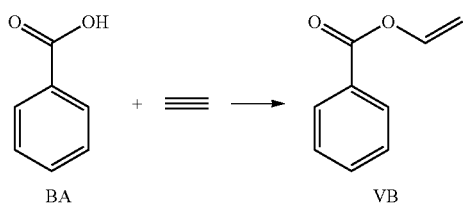

Similarly, when R is 2-ethylpentyl, the acid employed is 2-ethylhexanoic acid (2EHA) and the product formed is vinyl 2-ethylhexanoate (V2EH) in accordance with the following chemical equation.

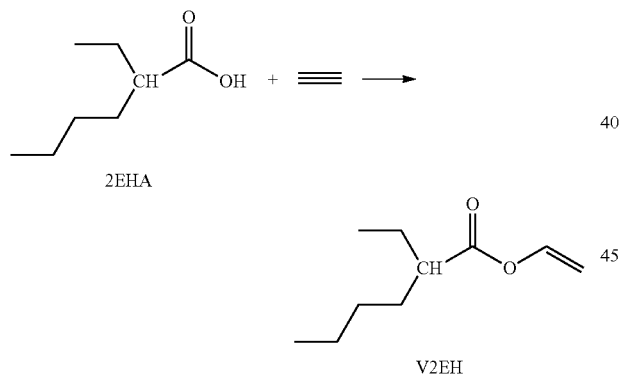

It has now been unexpectedly found that a vinyl ester can be made on an industrial scale from the reaction of a carboxylic acid with acetylene with high selectivity and yield. More particularly, this invention provides a homogeneous process for the selective formation of a vinyl ester from a carboxylic acid and acetylene comprising: reacting a carboxylic acid optionally dissolved in a suitable organic solvent with acetylene in the presence of a catalyst at a suitable reaction temperature and pressure, and optionally in the presence of one or more ligands or additives or a mixture thereof. Such solvents may include, for example, acetonitrile, butyl benzoate, diethyleneglycoldibutylether, mesitylene, mineral oil, toluene, and xylene.

Various carboxylic acids known in the art can be employed in the process of this invention to form corresponding vinyl esters. Illustrative of suitable carboxylic acids for the practice of the invention are aliphatic or aromatic monocarboxylic, dicarboxylic and polycarboxylic acids. Examples of aliphatic monocarboxylic acids include the following: acetic acid, propionic acid, butyric acid, valeric acid, hexanoic acid, heptanoic acid, octanoic acid, nonanoic acid, decanoic acid, 2-methylpropionic acid, 2-methylbutyric acid, 3-methylbutyric acid, 2-methylpentanoic acid, 2-ethylhexanoic acid, 2-propyl heptanoic acid; pivalic acid and other neo acids such as neodecanoic acid, neotridecanoic acid and neononanoic acid; stearic acid, and fatty acids. Examples of aromatic mono- and di-carboxylic acids include the following: benzoic acid, terephthalic acid, isophthalic acid and phthalic acid. Other aromatic carboxylic acids include substituted benzoic acid, such as for example, o-, m-, or p-toluic acid, o-, m-, or p-chlorobenzoic acid, and the like. Examples of aliphatic di- and polycarboxylic acids include: adipic acid, succinic acid, malic acid, maleic acid and polyacrylic acids. Various other carboxylic acids that are suitable in the process of this invention include crotonic acid, acrylic acid, methacrylic acid, salicylic acid, cinnamic acid, and cyclohexanoic acid.

Preferably, the acids that can be employed in the process of this invention include benzoic acid and various branched aliphatic carboxylic acids, such as for example 2-ethylhexanoic acid, 2-methylhexanoic acid, 2-ethylheptanoic acid, and the like.

Another particular class of carboxylic acids that are suitable in this invention is the neo acids. Neo acids are highly branched aliphatic carboxylic acids. In general, neo acids are trialkyl acetic acids, which include a tetra substituted alpha-carbon. Alkyl groups on the substituted alpha-carbon create a steric effect, i.e. hinder the ability of the neo acid to react. Methyl substituted alpha-carbon neo acids are the least hindered of the neo-acids. The reactivity of the neo acid primarily depends on the molecular weight and structure of the neo acid. In general, the greater the molecular weight of the alkyl groups on the alpha-carbon, the greater the steric effect and the less reactive the neo acid. The neo acids that are suitable in this invention may be expressed according to formula I:

Formula I

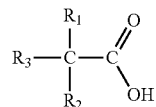

where each of $R_1$, $R_2$ and $R_3$ is an alkyl group having from 1 to 10 carbons and the total carbons in $R_1+R_2+R_3$ is from 3 to 30. Examples of neo acids include without any limitation neopentanoic acid, neoheptanoic acid, neodecanoic acid, etc. Several of the neo acids are commercially available, for example from ExxonMobil Chemical Company. Specific examples of commercially available neo acids include the ones listed above and proprietary neo acids such as neo 910 and neo 913 from ExxonMobil Chemical Company.

Although the process of this invention is intended to make vinyl ester from the reaction of acetylene with a carboxylic acid, various other known primary alkynes that can bring about such a vinylation reaction can also be employed in the process of this invention. Generally, unsubstituted alkynes and mono-substituted alkynes that do not interfere with the addition reaction of the process of this invention may be used. Representative substituents include alkyl, alkoxy, aryl, aryloxy, acetoxy, carboxyl and halo groups. Alkynes typically have from 2 to 10 carbon atoms and suitable alkynes include substituted or unsubstituted primary alkynes such as acetylene, methyl acetylene, phenyl acetylene, 1-butyne, 1-pentyne, 1-hexyne, 1-heptyne, 1-octyne, 1-nonyne, 1-decyne, and the like. More suitable alkynes useful in the practice of the invention include acetylene and methyl acetylene.

The catalyst employed in the process of this invention is a metal complex. Examples of metal complexes that are suitable in this process of the invention include without any limitation iridium, palladium, platinum, rhenium, rhodium and ruthenium.

It has now been found that the use of certain ligands and additives may enhance the catalytic activity of the catalysts of this invention. Various ligands and additives that can bring about the vinylation reaction with a carboxylic acid and acetylene can be employed in the process of this invention. Examples of ligands include without any limitation the following: triphenylphosphine, 1,2-diphenylphosphinobenzene (1,2-DPPB), o-bipyridyl, (±)-2,2'-bis(diphenyl-phosphino)-1,1'-binaphthalene, 1,1'-bis(diphenylphosphino)ferrocene, 4,5-bis (diphenylphosphino)-9,9-dimethylxanthene, diphenyl-2-pyridylphosphine, oxydi-2,1-phenylenebis(diphenylphosphine), tris(p-trifluoromethylphenyl)-phosphine [$P(p-CF_3C_6H_4)_3$], tris(1-naphthyl)phosphine, tris(2,4,6-trimethoxyphenyl)phosphine and tris(4-methoxyphenyl)phosphine.

Examples of additives include aluminum acetylacetonate, aluminum chloride, cadmium acetylacetonate, cerium chloride, iron chloride, potassium acetate, lithium acetate, lithium bromide, lithium chloride, sodium benzoate, sodium phosphate, sodium tetrafluoroborate, sodium chloride, sodium iodide, sodium trifluoroacetate, para-benzoquinone, palladium acetate, palladium acetylacetonate, palladium chloride, vinyl acetate, triruthenium dodecacarbonyl ($Ru_3(CO)_{12}$), zinc bromide, zinc chloride, benzoic anhydride, tri-(n-butyl) amine, tetra-(n-butyl)ammonium chloride, sodium phosphate and tetrabutylammonium acetate.

The process according to the invention may be practiced using a conventional reactor known in the art, under batch, semi-batch, or continuous conditions. For example, a continuous stirred-tank reactor (CSTR) with an elaborate acetylene vent system or a co-current or counter-current plug-flow reactor (column type) may be used, but these examples are not meant to be limiting. Typically, a homogeneous catalyst is recovered and returned to the reactor. In a batch system, a separate unit may periodically separate catalyst from the crude product between batches. In a continuous system, catalyst separation and recycle is preferably performed continuously. Alternatively, the homogeneous catalyst could be applied to a substrate to heterogenize the catalyst if so desired.

Any continuous acetylene reactor requires a large recycle stream for the unreacted gas, big compression systems and at the same time good control of the homogeneous catalyst via continuous addition through the carboxylic acid feed. At the same time, some crude liquid product should be withdrawn from the reactor.

One of skill in the art would likely select a reactor size necessary to optimize reactor throughput by whatever variable is appropriate, for instance reactor productivity (STY) or conversion.

In accordance with the invention, reaction of a carboxylic acid with acetylene can be carried out in a variety of configurations, including a batch reactor involving a single reaction zone.

As apparent from the Examples that follow, by practice of this invention it is possible to obtain high conversion and selectivity to vinyl esters such as VB. That is, by suitable selection of the catalyst and optionally the ligand(s) and additive(s) it has now been found that high conversion of carboxylic acid to vinyl ester can be achieved. More particularly, it has been observed that utilization of a desirable amount of catalyst in combination with optional ligand(s) and additive(s) results in at least 50 percent (%) conversion of carboxylic acid. Additionally, the selectivity to vinyl ester is found to be at least 50 percent (%). Furthermore, by suitable practice of this invention it is possible to attain a Relative Activity of at least 80 and up to about 2000.

The process of this reaction can be carried out using any reaction temperature such that the intended reaction of carboxylic acid with acetylene to form a vinyl ester can take place resulting in high selectivity to vinyl ester and at high conversions of carboxylic acid. Typically, such reactions are carried out at a temperature range of from about 40° C. to about 180° C. For example, the reaction temperature can range from about 40° C. to about 60° C. under certain catalytic conditions. The reaction temperature can also range from about 70° C. to about 90° C. under certain other catalytic conditions. In some cases the reaction temperature ranges from about 80° C. to about 100° C. In certain other situations the reaction temperature ranges from about 110° C. to about 130° C. In a few other situations, the reaction temperature may also range from about 130° C. to about 150° C. Finally, the reaction temperature ranges from about 150° C. to about 170° C. in some cases.

The reaction can also be carried out at any pressure condition so as to selectively form vinyl ester from a carboxylic acid at high conversions, such as for example sub-atmospheric, atmospheric or super-atmospheric conditions. Generally, it is preferred that the reaction is carried out at a pressure in the range of from about one atmosphere to two atmospheres absolute. More particularly, the reaction is carried out at atmospheric pressure conditions in an inert atmosphere, such as for example in an atmosphere of nitrogen, helium or argon.

In general, the amount of acetylenic compound employed is equimolar or slightly in excess of equimolar to the carboxylic group to be converted. Thus, when the carboxylic acid used is a mono-carboxylic acid, a molar ratio of acetylene to acid is generally from about 1:1 to 100:1, preferably from about 1.2:1 to 30:1, and more preferably from about 1.5:1 to about 10:1. Accordingly, acetylenic compound is proportionately used in higher quantities when dibasic and/or other polybasic acids are employed.

In an aspect of this invention, the process of this invention can be carried out with a small amount of the catalyst. That is, large amounts of carboxylic acid, such as benzoic acid (BA) can be converted to a vinyl ester (i.e., VB) in the presence of small amounts of catalyst material. Generally, the reaction mixture comprises a mixture of desired metal complex catalyst and a carboxylic acid (CA) in a molar carboxylic acid to metal ratio of from about 4000:1 to about 100:1.

More typically, the molar CA/metal ratio is about 1000:1. However any other molar CA/metal ratio that would bring about the desired conversion and selectivity to vinyl ester can be employed in the process of this invention.

In another aspect of this invention, the catalyst exhibits a very high Relative Activity (moles of vinyl ester/metal atom) in the process of this invention. Typically, the Relative Activities range from about 100 to about 1000.

In a further aspect of this invention, very high selectivity to vinyl ester, such as for example vinyl benzoate, can be obtained by suitable practice of the process of this invention. Typically, the selectivity to vinyl ester based on benzoic acid consumed can at least be 60 percent. More specifically, the selectivity to vinyl ester based on carboxylic acid consumed may be at least 80 percent. Even more specifically, the selectivity to vinyl ester based on carboxylic acid consumed is at least 99 percent.

The process of this invention can be carried out to a desirable length of time in order to obtain the best catalyst activity, Relative Activities and selectivity to VE. Typically, the reactions are run in a batch mode for a period ranging from about 1 hour to about 5 hours. More typically, the reaction is carried out in the batch mode for a period of about four hours. However, the process of this invention can be carried out in a semi-continuous or continuous manner using any of the known process techniques in the art.

In one of the embodiments of the process of this invention the catalyst utilized is a platinum metal complex. Various known platinum metal complexes can be employed in the process of this invention. Examples of platinum metal complexes include without any limitation the following: platinum acetyl-acetonate, (1,5-cyclooctadiene)-dimethylplatinum (II), platinum(II) iodide, platinum(IV) iodide, platinum(II) bromide, platinum(IV) bromide, platinum(II) chloride, platinum(IV) chloride, platinum(0)-2,4,6,8-tetramethyl-2,4,6,8-tetravinylcyclotetrasiloxane, platinum(0)-1,3-divinyl-1,1,3,3-tetramethyl-disiloxane in xylene and cis-bis(benzonitrile)-dichloroplatinum(II). The addition of certain ligands improves the activity of the platinum catalyst which activity can generally be measured by the increase in observed Relative Activity of the reaction. Particularly an additive 4,5-bis(diphenylphosphino)-9,9-dimethyl-xanthene is found to enhance both the conversion of carboxylic acid and the selectivity to vinyl ester, such as vinyl benzoate.

The platinum catalysts as described herein may also be used in conjunction with one or more other ligands as described herein. Particularly suitable ligands other than the one described above for the platinum catalysts without any limitation are the following: 1,2-DPPB, triphenylphosphine and oxydi-2,1-phenylenebis(diphenylphosphine). The reaction with platinum catalysts can be carried out with any of the solvents described herein, butyl benzoate being the most suitable solvent. However, in certain situations, the reaction can be carried out without a solvent. For instance, if a carboxylic acid employed is an aliphatic carboxylic acid, and since most of them are liquids at room temperature, these acids can be employed in this process without any solvent. For example, if the acid employed is 2-ethylhexanoic acid there is no need to use any solvent.

The reaction utilizing platinum catalyst can suitably be carried out at a temperature in the range of from about 80° C. to about 180° C. More preferably in the temperature range of from about 120° C. to about 160° C. In particular, the reaction temperature of from about 140° C. to 160° C. is found to provide high Relative Activities, however, any of the other temperature ranges as described herein may also be suitable. The Relative Activities for platinum catalysts generally range from about 450 to about 900, preferably the Relative Activities range from about 500 to about 850. The selectivity to vinyl ester using platinum catalysts range from about 50 percent to about 100 percent, preferably the selectivity range from about 70 percent to about 100 percent and more preferably the selectivity range from about 80 percent to about 100 percent.

In another aspect of the process of this invention, the suitable catalyst for the process of this invention is a rhenium metal complex catalyst. Any of the known rhenium complexes that will be effective in the process of this invention can be used. Examples of rhenium metal catalysts that are suitable for the process of this invention include without any limitation, bromopentacarbonylrhenium (I), pentacarbonylchlororhenium (I) and dirheniumdecacarbonyl. As described herein the rhenium catalysts can further comprise one or more ligands so as to enhance the catalyst activity. Examples of suitable ligands for rhenium catalysts include 4,5-bis(diphenylphosphino)-9,9-dimethylxanthene or oxydi-2,1-phenylenebis-(diphenylphosphine). In addition, one or more of the additives as described herein can be used with rhenium catalysts. An example of an additive that is suitable with rhenium metal catalyst is potassium acetate or sodium benzoate.

In one embodiment of the process of this invention the metal complex catalyst employed is dirhenium decacarbonyl alone or in combination with a ligand, which is 4,5-bis(diphenylphosphino)-9,9-dimethylxanthene or oxydi-2,1-phenylenebis(diphenylphosphine). In another embodiment of the process of this invention the metal complex catalyst employed is (acetonitrile)trichlorobis-(triphenylphosphine)-rhenium (III), methyltrioxorhenium(VII) or iododioxo-bis (triphenylphosphine)-rhenium(V).

The rhenium catalysts are particularly found to be suitable catalysts in the process of this invention. Particularly preferred rhenium catalysts are pentacarbonylchloro-rhenium (I) and dirheniumdecacarbonyl. The rhenium catalysts generally result in very high conversion of carboxylic acid to vinyl ester, such as for example BA to VB. Typically the conversion is at least about 80 percent and more typically the conversion is at least about 95 percent. Similarly, the selectivity to vinyl ester is also high with rhenium catalysts. Typically, selectivity to vinyl ester is at least about 80 percent, more typically, it is at least about 95 percent. The turn-over-numbers are also high with rhenium catalysts. Typically, a Relative Activity of at least about 400 is attainable with rhenium catalysts. The reaction with rhenium catalysts can be carried out with any of the solvents described herein, butyl benzoate being the most suitable solvent.

The reaction in the presence of a rhenium catalyst can suitably be carried out at a temperature in the range of from about 80° C. to about 180° C. More preferably in the temperature range of from about 120° C. to about 160° C. In particular the reaction temperature of about 140° C. is found to provide high Relative Activities, however, any of the other temperature ranges as described herein may also be suitable. The reaction with rhenium catalysts are again carried out typically in a batch mode for a period of about 2 to 4 hours. However, any of the known semi-continuous or continuous process conditions can also be employed with rhenium catalysts. In the presence of rhenium catalysts very high molar carboxylic acid (CA)/metal ratio can be employed. For example, molar CA/rhenium metal ratio of about 350 to 1200 can be employed resulting in very high selectivity to VE. For example, at very high molar CA/metal ratio of about 1200, selectivity to VE of up to 99 percent can be attained.

In another aspect of the process of this invention, the metal complex catalyst employed is a rhodium metal complex catalyst. Any of the known rhodium complexes that will be effective in the process of this invention can be used. Examples of rhodium complex catalysts include the following:
(acetylacetonato)dicarbonylrhodium(I),
1,1'-bis(diisopropylphosphino)ferrocene(cod)Rh-phosphotungstic acid,
[1,4-bis(diphenylphosphino)butane](1,5-cyclooctadiene) rhodium (I) tetrafluoroborate,
bis(1,5-cyclooctadiene)dirhodium(I)dichloride,
tetrarhodium dodecacarbonyl,
dichloro(pentamethylcyclopentadienyl)rhodium(III) dimer,
methoxy(cyclooctadiene)rhodium(I) dimer, and
rhodium (II) acetate dimer.

The rhodium catalysts can again be used in combination with one or more ligands as described herein. Examples of suitable ligands for rhodium catalysts are the following:

1,1'-bis(diphenylphosphino)ferrocene,
tris(p-trifluoromethylphenyl)phosphine,
tris(1-naphthyl)phosphine,
tris(2,4,6-trimethoxyphenyl)phosphine,
tris(4-methoxyphenyl)phosphine,
oxydi-2,1-phenylenebis(diphenylphosphine),
diphenyl-2-pyridylphosphine,
1,2-diphenylphosphinobenzene (1,2-DPPB),
Triphenylphosphine, and
4,5-bis(diphenylphosphino)-9,9-dimethylxanthene.

In addition, use of one or more additives as described herein in combination with rhodium catalysts may improve over all selectivity and conversion to VE. Specific examples of additives include sodium tetrafluoroborate among others.

More particularly, the following combination of a rhodium metal complex catalyst and a ligand can be employed in order to obtain optimum results:

tetrarhodium dodecacarbonyl and oxy-di-2,1-phenylenebis-(diphenylphosphine);
tetrarhodium dodecacarbonyl and diphenyl-2-pyridylphosphine;
rhodium acetate dimer and 1,2-DPPB;
rhodium acetate dimer and triphenylphosphine;
rhodium acetate dimer and 4,5-bis(diphenylphosphino)-9,9-dimethylxanthene;
rhodium acetate dimer and oxydi-2,1-phenylenebis(diphenyl-phosphine);
(acetylacetonato)carbonyl(triphenylphosphine)rhodium (I) and triphenylphosphine; and
bis(1,5-cyclooctadiene)dirhodium (I) dichloride, triphenylphosphine and sodium tetrafluoroborate as an additive.

In general, the rhodium catalysts exhibit high Relative Activities at a reaction temperature in the range of from about 50° C. to about 180° C., more particularly at a temperature range of from about 120° C. to about 160° C. The Relative Activities typically increase with increasing temperature and range from about 50 to about 300. In particular, a Relative Activity of at least 100 is observed at a reaction temperature in the range of about 160° C. Any of the solvents as described herein can be employed in the presence of rhodium catalysts; acetonitrile, toluene and butyl benzoate being more advantageous. It is also observed that use of any of the ligands as described herein and more particularly the ones described with rhodium catalysts improves the Relative Activities as well as selectivity to VE. More notably, for rhodium catalysts, such as rhodium(II) acetate dimer, the addition of ligands considerably improves the activity of the catalyst. Particularly, the addition of mono- or bi-dentate aromatic phosphine ligands, as described herein, improves the activity of rhodium catalysts for the production of VE. For example, highest Relative Activity can be achieved by a combination of rhodium(II) acetate dimer with the bidentate ligand oxydi-2,1-phenylenebis(diphenylphosphine). In general, the conversion of carboxylic acid and selectivity to VE also increases with increasing temperature from about 50° C. to about 180° C.

In another aspect of the process of this invention, the metal complex catalyst is ruthenium. Any of the known ruthenium complexes that will be effective in the process of this invention can be used. Examples of ruthenium metal complexes include the following: bis(2-methylallyl)(1,5-cyclooctadiene)-ruthenium (II) and triruthenium dodecacarbonyl. The ruthenium catalysts can again be used in combination with one or more suitable ligands as described herein. Suitable ligands that may be used with ruthenium include the following: 1,2-diphenylphosphino benzene (1,2-DPPB), triphenylphosphine and tris(4-methoxyphenyl)phosphine. In addition, the ruthenium catalysts can also be used in combination with one or more additives as described herein.

Representative examples of a combination of ruthenium catalyst and a ligand include the following: bis(2-methylallyl)(1,5-cyclooctadiene)ruthenium (II)/1,2-diphenylphosphino benzene (1,2-DPPB); triruthenium dodecacarbonyl-/triphenyl-phosphine; and triruthenium dodecacarbonyl/1,2-DPPB. The reaction with ruthenium catalysts can be carried out in any of the solvents as described herein, butyl benzoate being preferred when the reaction temperature is higher than 120° C. However at lower temperatures acetonitrile (around a reaction temperature of about 50° C.) or toluene (around a reaction temperature of about 80° C. or 90° C.) may be used. At a reaction temperature higher than 120° C., mesitylene can also be used as a solvent. The reaction with rhodium catalysts is preferably carried out at a temperature range of from about 50° C. to about 180° C. The selectivity to VE generally increases with an increase in temperature. However, in the presence of the ligands 1,2-DPPB or triphenylphosphine, the selectivity slightly decreases at higher temperatures. However, in general higher temperatures have a positive effect for the catalyst triruthenium dodecacarbonyl in the presence of 1,2-DPPB or triphenylphosphine.

In another aspect of the process this invention the metal complex catalyst is palladium. Any of the known palladium complexes that will be effective in the process of this invention can be used. Examples of palladium metal complexes include the following: palladium (II) acetate and palladium (II)[1,3-bis(diphenyl-phosphino)propane]-bis(benzonitrile)-bis-tetrafluoroborate. Again, various ligands as disclosed herein which can be used in combination with palladium can be employed in this aspect of the invention. Both mono- and bidentate ligands can be employed. Specific examples of such bidentate ligands include without any limitation (±)-2,2'-bis(diphenylphosphino)-1,1'-binaphthalene, 4,5-bis(diphenylphosphino)-9,9-dimethylxanthene, and 1,1'-bis(diphenylphosphino)-ferrocene. Examples of monodentate ligands include: diphenyl-2-pyridyl-phosphine, tris(1-naphthyl)phosphine and oxydi-2,1-phenylenebis(diphenyl-phosphine). Other ligands such as 1,2-diphenylphosphinobenzene (1,2-DPPB) or tris(1-naphthyl)phosphine can also be employed with palladium catalysts.

Typically, any combination of palladium metal complex optionally in combination with a ligand may be employed. More preferably, a combination of palladium acetate with 1,2-DPPB has been found to be an effective catalyst in order to produce VE with high Relative Activities. The reaction is generally carried out at any of the temperature ranges disclosed herein. Preferably the reaction is carried out at temperature range of from about 60° C. to about 180° C., preferably at about 150° C. to about 170° C. Relative Activities typically range from about 100 to about 200, more preferably from about 140 to about 160. Toluene or butyl benzoate are the preferred solvents. In general, the amount of vinyl ester, such as vinyl benzoate produced is higher at a temperature in the range of about 110° C. to 130° C. Also, the conversion and the selectivity increase with temperature for the palladium catalyst combinations as disclosed herein. In general, the addition of ligands to palladium acetate improved the catalytic activity, thereby improving the production of VE. Both mono- and bidentate ligands show positive effect on the catalytic activity of palladium acetate.

In another aspect of the process this invention, the metal complex catalyst is iridium. Any of the known iridium complexes that will be effective in the process of this invention can be used. Examples of iridium metal complexes include the following: 1,5-cyclooctadiene(hexafluoroacetylacetonato) iridium (I), (acetylacetonato) (1,5-cyclooctadiene)iridium(I) and iridium(III)acetylacetonate. The reaction can be carried out at any of the temperature ranges as described herein, preferably at a range of from about 40° C. to about 180° C. More preferably, the reaction temperature is in the range of from about 50° C. to about 120° C. Generally, the amount of vinyl ester, such as vinyl benzoate produced increases with increasing temperature up to 120° C., depending upon the catalyst employed. However, when iridium(III)acetylacetonate is employed as the catalyst, the highest production of VE is observed at 160° C.

In general, the selectivity to VE also increases with increasing temperature up to 120° C. for most iridium catalysts. However, when iridium(III)acetyl-acetonate is employed, the selectivity to VE increases as the temperature increases up to 160° C.; the conversion similarly increases as discussed above. The selectivity and conversion of VE can also be increased with increasing CA/iridium molar ratio, thereby increasing the Relative Activities. The addition of ligands in the case of iridium catalysts exhibited a negative effect on the activity of iridium catalysts, thus providing no beneficial effect.

In an embodiment of this invention, there is also provided a homogeneous process for the selective formation of vinyl benzoate from benzoic acid using a platinum catalyst. In this embodiment of the process of this invention, benzoic acid is reacted with acetylene in a suitable organic solvent. Suitable solvents include the ones described herein. Preferably toluene or butyl benzoate is used at reaction temperatures higher than 90° C. and acetonitrile is used below reaction temperature of 90° C. Mineral oil can also be used as a solvent in place of butyl benzoate. The reaction is generally carried out at a temperature in the range of about 40° C. to about 160° C., preferably at a temperature in the range of about 100° C. to 160° C. Generally, increasing the temperature produces higher amount of vinyl benzoate especially with certain platinum catalysts. The reaction is generally carried out in the presence of a platinum catalyst chosen from platinum m acetylacetonate, platinum iodide, platinum bromide or (1,5-cyclooctadiene)-dimethylplatinum(II). In general, higher amounts of vinyl benzoate are produced at 160° C. compared to 120° C. when platinum acetylacetonate or platinum bromide is used as a catalyst. However, an increase of temperature from about 120° C. to about 160° C. may not have significant effect on the conversion of benzoic acid to vinyl benzoate with other platinum catalysts. It has also been observed that use of certain ligands in combination with the platinum catalysts enhances the catalytic activity. Examples of ligands that can be employed include 4,5-bis(diphenyl-phosphino)-9,9-dimethylxanthene, oxydi-(2,1-phenylene) bis(diphenylphosphine) or triphenylphosphine.

It has also been observed in general that the conversion and selectivity trends with temperature are related to a specific catalyst system, i.e., a combination of the catalyst and ligands. For example, the conversion of benzoic acid decreases and the selectivity to vinyl benzoate increases with the increasing temperature when platinum iodide is employed alone or with 4,5-bis(diphenyl-phosphino)-9,9-dimethylxanthene. On the other hand, no significant change of benzoic acid conversion is observed for (1,5-cyclooctadiene)dimethylplatinum(II) and for platinum acetylacetonate when tested with oxydi-2,1-phenylenebis-(diphenylphosphine), but the selectivity to vinyl benzoate decreases with the increasing temperature.

In another embodiment of the process of this invention, there is also provided a homogeneous process for the selective formation of vinyl benzoate from benzoic acid using a rhenium catalyst. In this embodiment of the process of this invention benzoic acid is reacted with acetylene in a suitable organic solvent. Suitable solvents include the ones described herein. Preferably toluene or butyl benzoate is used at reaction temperatures higher than 90° C. and acetonitrile is used below reaction temperature of 90° C. The reaction is generally carried out at a temperature in the range of about 40° C. to about 160° C., preferably at a temperature in the range of about 100° C. to 160° C. Generally, the highest selectivity to vinyl benzoate is obtained at around a reaction temperature of about 140° C. with a rhenium catalyst combined with ligands. The reaction is generally carried out in the presence of a rhenium catalyst chosen from pentacarbonylchlororhenium (I), di-rhenium decacarbonyl, or bromopentacarbonylrhenium (I). Generally, the reaction is further carried out in combination with a ligand chosen from 4,5-bis(diphenylphosphino)-9,9-dimethylxanthene, oxydi-(2,1-phenylene)bis-(diphenylphosphine), and optionally including as an additive potassium acetate or sodium benzoate.

FIG. 1 illustrates a laboratory scale system 10 for the production of vinyl esters by the reaction of a carboxylic acid and acetylene using the catalyst system of this invention. The system 10 of FIG. 1 comprises a stirred reactor 20 and a collector 30. The reactor 20 and the collector 30 are each provided with a condenser 40, 50 for which a conventional means of pressure regulation is provided, such as a bubbler, not shown. Briefly, a suitable reactor 20 of desired size, such as a 250 mL three-neck glass flask, is employed. The reactor 20 is initially charged via line 22 with a desired carboxylic acid, suitable solvent and predetermined amounts of catalyst, and if necessary, ligands and additives. Then the reactor 20 is purged with nitrogen and heated to desired reaction temperature. Acetylene is then bubbled into the reaction mixture at a desired rate via line 24 and additional carboxylic acid may be charged, with solvent as necessary, via line 22. As the reaction proceeds, the vinyl ester product is removed via line 26 and is fractionated and collected in a collection flask 30. The condensers 40, 50 serve to recover an optimal amount of product and solvent while releasing non-condensible gases. The temperature of the condensers 40, 50 is regulated by conventional means known to one of skill in the art. The order of addition of the reactants is not crucial in the process of this invention.

EXAMPLES

The following examples are presented to further illustrate the present invention and should not be taken as limiting the invention, the spirit and scope of which is set forth in the appended claims. These examples are provided for illustrative purposes only and various modifications thereof can readily be made which are known to one skilled in the art.

Figure 2:
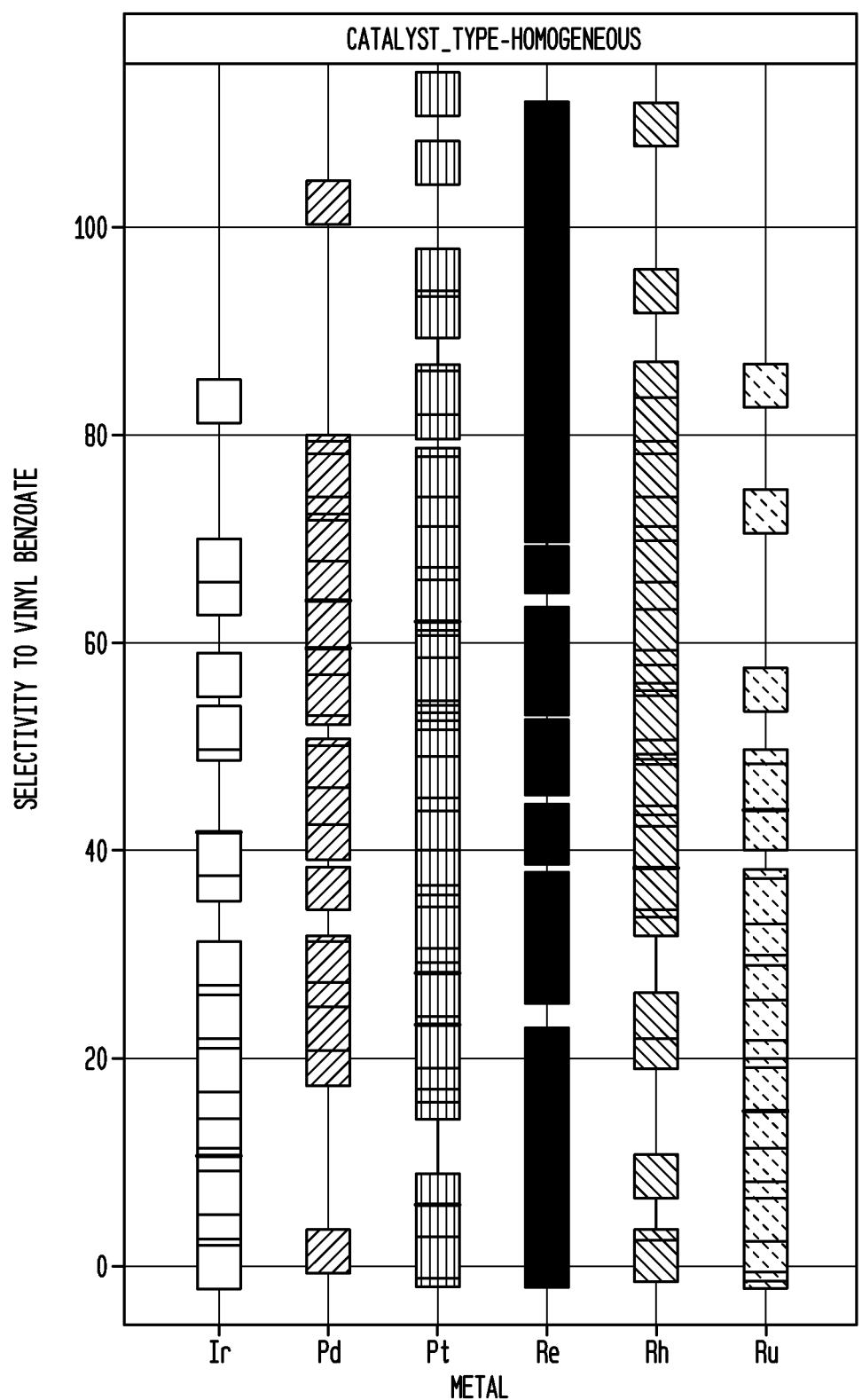
FIG. 2 is an illustration of the relative selectivity to vinyl benzoate achieved using a variety of catalyst metals according to the process of the invention.
Figure 3:
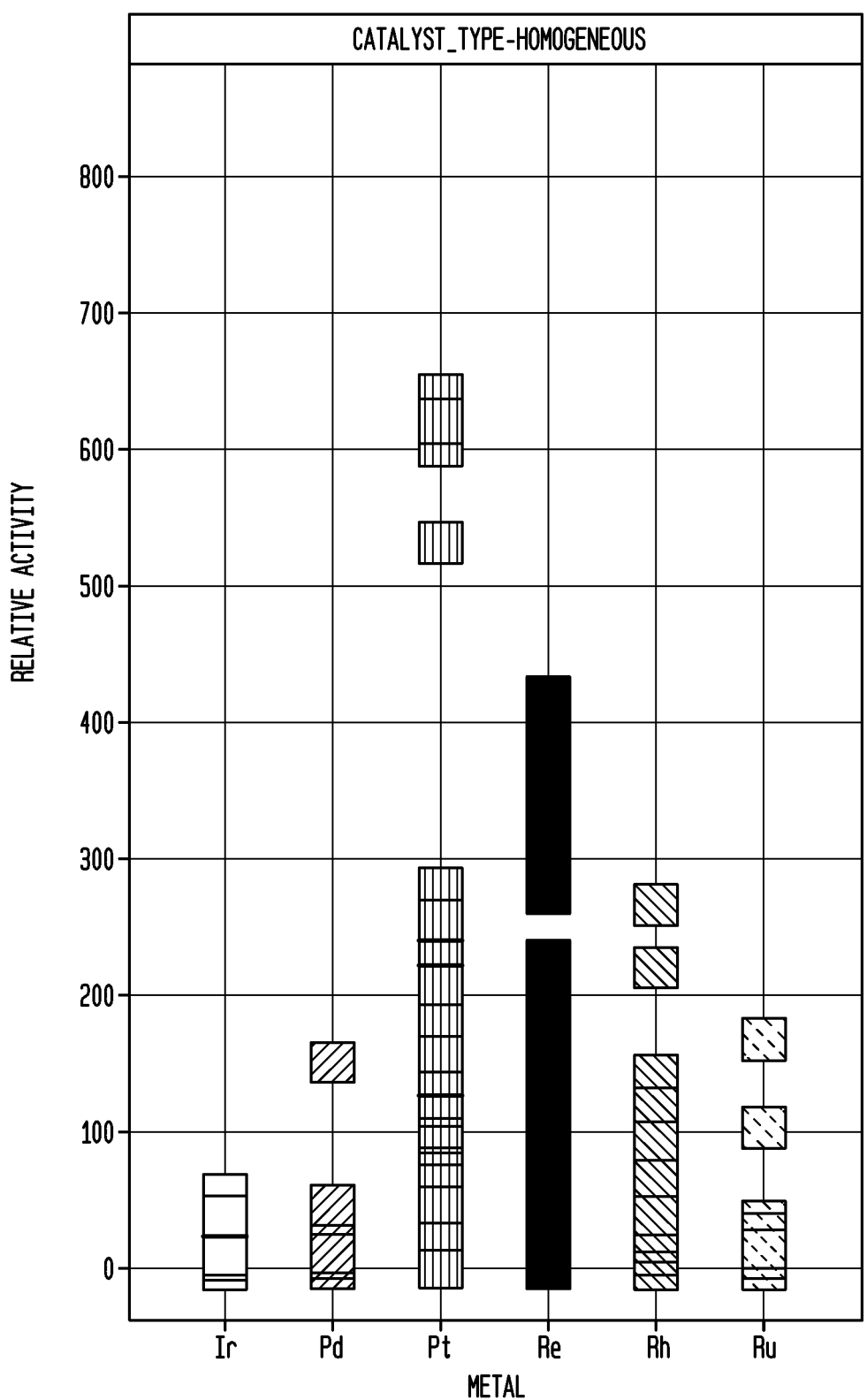
FIG. 3 is an illustration of the Relative Activity achieved using a variety of catalyst metals according to the process of the invention.

Examples 1-23 illustrate the conversion of benzoic acid to vinyl benzoate using various catalysts of this invention. The selectivity to vinyl benzoate and TONs achieved by Examples 1 and 3-23 are displayed in summary form in FIGS. 2 and 3, respectively.

Specifically, Examples 1-6 illustrate the catalytic activity of various platinum metal complexes with or without ligands and/or additives. Examples 7-11 illustrate the catalytic activity of various rhenium metal complexes with or without ligands and/or additives. Examples 12 and 13 illustrate the catalytic activity of various rhodium metal complexes with or without ligands and/or additives. Examples 14-17 illustrate the catalytic activity of various ruthenium metal complexes with or without ligands and/or additives. Examples 18-20 illustrate the catalytic activity of various palladium metal complexes with or without ligands and/or additives. Examples 21-23 illustrate the catalytic activity of various iridium metal complexes with or without ligands and/or additives.

Examples 24-33 illustrate the conversion of 2-ethylhexanoic acid to vinyl 2-ethylhexanoate using various catalysts of this invention. Examples 34-43 illustrate the conversion of various other carboxylic acids including neo acids to corresponding vinyl ester using various catalysts of this invention.

Finally, Comparative Examples 1-5 illustrate the catalytic activity of prior art catalysts such as zinc and cadmium catalysts for the production of vinyl benzoate under comparative reaction conditions.

Table 1 summarizes various catalysts and ligand complexes that can be used in the process of this invention to produce VE selectively as described herein. Also listed are the selectivity to VE and TONs that can be attained using these catalyst systems. The Examples that follow provide more detailed results.

TABLE 1

Catalyst screening results within noble metal group

| Metal | Catalyst/Ligand Complexes | Vinyl Ester Selectivity (%) | TON |
|---|---|---|---|
| Ru | bis(2-methylallyl)(1,5-cyclooctadiene)ruthenium(II)/1,2-DPPB Triruthenium dodecacarbonyl/PPh$_3$ or 1,2-DPPB | 25-75 | >100 |
| Rh | Acetylacetonatocarbonyltriphenyl-phosphinerhodium(I)/PPh$_3$ bis(1,5-cyclooctadiene)dirhodium(I) dichloride/PPh3/NaBF$_4$ | 60-100 | >100 |
| Pd | palladium(II)acetate/4,5-bis(diphenylphosphino)-9,9-dimethylxanthene Palladium(II)[1,3-bis(diphenylphosphino)propane]-bis(benzonitrile)-bis-tetrafluoroborate | 76 | >100 |
| Re | Pentacarbonylchlororhenium(I) Dirhenium decacarbonyl | >95 | 420 |
| Ir | (acetylacetonato)(1,5-cyclooctadiene)Ir(I) 1,5-cyclooctadiene (hexafluoroacetylacetonato)iridium(I) | ~50 | ~50 |
| Pt | Platinum acetylacetonate (1,5-cyclooctadiene)dimethylplatinum(II) | 80-100 | 500-640 |

Gas Chromatographic (GC) Analysis of the Products

The following procedure illustrates specific GC method that can be used for the conversion of benzoic acid (BA) to vinyl benzoate (VB). Similar methods can be readily set-up for other vinyl esters.

The analysis of the products was carried out by GC using a DB-FFAP 0.25 micron column (30 m×0.25 mm) A backflush column CP-Sil 5 (1 m×0.25 mm) was installed to prevent high boiling solvents being analyzed on the main column. The GC samples were generally prepared as follows. A final reaction mixture containing the reactant and product(s) (~1 mL) was diluted with toluene (4 mL) containing a precise quantity of dodecane (the internal standard). The total mixture was stirred for either 5 or 30 minutes at room temperature in order to dissolve the reactant and product(s). The 0.04 mL final sample was further diluted with toluene to ensure correct concentration ranges for the GC analysis. In some cases, the reaction mixture was diluted with 5 mL of toluene and stirred at room temperature for one hour to dissolve the reactant and product(s).

The peaks of benzoic acid and vinyl benzoate were well separated from other peaks. Dodecane was used as the external standard, which was well separated from other peaks in the chromatograph. The GC was calibrated for benzoic acid and vinyl benzoate by analyzing a set of calibration mixtures. The GC method was sensitive enough to detect 25 ppm of benzoic acid and 5 ppm of vinyl benzoate. The following temperature profile was used in this GC method: 50° C., hold time 1 minute, ramp at 20° C./min to 160° C., hold time 0 minute, ramp at 40° C./minute to 250° C., hold time 2.25 minute–the total duration of the run=11 minutes.

Example 1

A suitable reactor vessel equipped with appropriate inlets and stirring device was charged with 360 milligrams of benzoic acid and 500 ppm of para-benzoquinone. The reactor was purged two to three times with nitrogen and a constant flow of nitrogen was maintained. To this mixture was added 900 milligrams of butyl benzoate with stirring and the mixture was heated slightly, if necessary, to dissolve benzoic acid. To this solution was added 3 milligrams of platinum acetylacetonate (a molar ratio of acid to catalyst metal of about 385) with stirring and the entire mixture was heated to 140° C. At this time, acetylene was fed into the reactor at a steady stream maintaining the pressure of acetylene at 1.7 bars. The reaction mixture was stirred for an additional 4 hour period. At the end of this period, a sample of the reaction mixture was removed and analyzed by GC as described above. From the GC analysis it was observed that the selectivity to vinyl benzoate was 55 percent. The conversion of benzoic acid was 60 percent and the TON was around 90-110.

Example 2

A suitable reactor vessel equipped with appropriate inlets and stirring device is charged with 17 grams of benzoic acid and 2 grams para-benzoquinone. The reactor is purged two to three times with nitrogen and a constant flow of nitrogen was maintained. To this mixture is added 142.5 grams of butyl benzoate with stirring and the mixture is heated slightly, if necessary, to dissolve benzoic acid. To this solution is added 8.5 grams of platinum acetylacetonate with stirring and the entire mixture is heated to 120° C. At this time, acetylene is fed into the reactor at a steady stream and at a rate of 100 mL/min. The reaction mixture is stirred for an additional 4 hour period. At the end of this period, a sample of the reaction mixture is removed and analyzed by GC as described above.

Example 3

Example 1 was substantially repeated in several runs using the following conditions. The reaction temperature was maintained at either 120° C. or 160° C. Butyl benzoate was used as a solvent. The amount of benzoic acid used was 100 milligrams in combination with 500 ppm of para-benzoquinone and 10 milligrams of platinum homogeneous catalyst. The observed results of TON and yield of VB are summarized in Table 2.

TABLE 2

| Catalyst | Temp. (° C.) | TON | Yield of VB (%) |
|---|---|---|---|
| (1,5-Cyclooctadiene)dimethylplatinum(II) | 120 | 7.5 | 27 |
| | 160 | 7 | 25 |
| Platinum acetylacetonate | 120 | 4.5 | 13 |
| | 160 | 13 | 43 |
| Platinum(II) bromide | 120 | 0.5 | 1 |
| | 160 | 4 | 12 |
| Platinum(II) chloride | 120 | 1 | 4 |
| | 160 | 0 | 1 |
| Platinum(IV) chloride | 120 | 2.5 | 8 |
| | 160 | 1.5 | 6 |
| Platinum(II) iodide | 120 | 8 | 20 |
| | 160 | 7.5 | 20 |

Example 4

Example 1 was substantially repeated in several runs using the following conditions. Three different reaction temperatures were employed: 120° C., 140° C. and 160° C. Butyl benzoate was used as a solvent. The amount of benzoic acid used was 360 milligrams in combination with 500 ppm of para-benzoquinone and appropriate amount of platinum homogeneous catalyst so as to maintain a similar molar BA/metal ratio as in Example 1. Various ligands were also used with each of the platinum metal complex as summarized in Table 3. Also summarized in Table 3 are the TONs, conversion and selectivity to VB.

TABLE 3

| Catalyst/Ligand | Temp. (° C.) | TON | Selectivity to VB (%) | Conv. (%) |
|---|---|---|---|---|
| (1,5-Cyclooctadiene)dimethylplatinum(II) | 120 | 9 | 50 | 55 |
| | 140 | 35-65 | 60 | 15-25 |
| | 160 | 90 | 55 | 45 |
| (1,5-Cyclooctadiene)dimethylplatinum(II)/4,5-Bis(diphenylphosphino)-9,9-dimethylxanthene | 120 | 50 | 45 | 33 |
| | 140 | 65 | 50 | 35 |
| | 160 | 65 | 55 | 32 |
| (1,5-Cyclooctadiene)dimethylplatinum(II)/Oxydi-2,1-phenylenebis(diphenylphosphine) | 120 | 40 | 50 | 22 |
| | 140 | 45-65 | 30-45 | 30-50 |
| | 160 | 22 | 20 | 30 |
| (1,5-Cyclooctadiene)dimethylplatinum(II)/triphenylphosphine | 120 | 30 | 20 | 30 |
| | 140 | 20-50 | 20-60 | 20-25 |
| | 160 | 38 | 20 | 30 |
| Platinum acetylacetonate | 120 | 120 | 50 | 60 |
| | 140 | 90-110 | 50-55 | 55-60 |
| | 160 | 100 | 55 | 45 |
| Platinum acetylacetonate/4,5-Bis(diphenylphosphino)-9,9-dimethylxanthene | 120 | 85 | 45 | 62 |
| | 140 | 60-85 | 45-50 | 40-50 |
| | 160 | 82 | 50 | 52 |
| Platinum acetylacetonate/Oxydi-2,1-phenylenebis(diphenylphosphine) | 120 | 45 | 40 | 38 |
| | 140 | 40-60 | 25-40 | 40-45 |
| | 160 | 80 | 38 | 58 |
| Platinum acetylacetonate/triphenylphosphine | 120 | 20 | 20 | 30 |
| | 140 | 30-50 | 30-80 | 10-55 |
| | 160 | 110 | 50 | 65 |
| Platinum(II) iodide | 120 | 30 | 20 | 75 |
| | 140 | 45-65 | 65-75 | 10-30 |
| | 160 | 65 | 65 | 25 |
| Platinum(II) iodide/4,5-Bis(diphenylphosphino)-9,9-dimethylxanthene | 120 | 20 | 20 | 35 |
| | 140 | 20 | 80 | 7 |
| | 160 | 20 | 95 | 8 |
| Platinum(II) iodide/Oxydi-2,1-phenylenebis(diphenylphosphine) | 120 | 10 | 60 | 3 |
| | 140 | 6-10 | 70 | 1-3 |
| | 160 | 7 | 90 | 1 |
| Platinum(II) iodide/triphenylphosphine | 120 | 0 | 40 | 0 |
| | 140 | 0 | 0 | 0 |
| | 160 | 0 | 0 | 0 |

Example 5

Example 1 was substantially repeated in several runs using the following conditions. The reaction temperature was maintained at 140° C. for all of the runs. Butyl benzoate was used as a solvent. The amount of benzoic acid used was 360 milligrams in combination with 500 ppm of para-benzoquinone. The necessary amount of platinum homogeneous catalyst was used to attain three different levels of molar BA/metal ratios of 385, 1155 and 3850. Various ligands were also used with each of the platinum metal complex as summarized in Table 4 with these varied molar BA/metal ratio. Also summarized in Table 4 are the TONs, conversion and selectivity to VB.

TABLE 4

| Catalyst/Ligand | BA/metal ratio | TON | Selectivity to VB (%) | Conv. (%) |
|---|---|---|---|---|
| (1,5-Cyclooctadiene)dimethylplatinum(II) | 385 | 35-65 | 60 | 15-25 |
| | 1155 | 180 | 60 | 38 |
| | 3850 | 600 | 65 | 35 |
| (1,5-Cyclooctadiene)dimethylplatinum(II)/4,5-Bis(diphenylphosphino)-9,9-dimethylxanthene | 385 | 45-65 | 50-55 | 25-30 |
| | 1155 | 180 | 65 | 25 |
| | 3850 | 520 | 60 | 25 |
| (1,5-Cyclooctadiene)dimethylplatinum(II)/Oxydi-2,1-phenylenebis(diphenylphosphine) | 385 | 65 | 45 | 50 |
| | 1155 | 200 | 55 | 30 |
| | 3850 | 200 | 60 | 10 |
| (1,5-Cyclooctadiene)dimethylplatinum(II)/triphenylphosphine | 385 | 15-35 | 20-60 | 20-25 |
| | 1155 | 100 | 45 | 20 |
| | 3850 | 180 | 45 | 12 |
| Platinum acetylacetonate | 385 | 90-110 | 50-55 | 55-60 |
| | 1155 | 220 | 60 | 50 |
| | 3850 | 650 | 75 | 23 |
| Platinum acetylacetonate/4,5-Bis(diphenylphosphino)-9,9-dimethylxanthene | 385 | 80 | 50 | 45 |
| | 1155 | 300 | 60 | 38 |
| | 3850 | 620 | 75 | 20 |
| Platinum acetylacetonate/Oxydi-2,1-phenylenebis(diphenylphosphine) | 385 | 40-50 | 25-40 | 40-45 |
| | 1155 | 170 | 45 | 28 |
| | 3850 | 200 | 60 | 9 |
| Platinum acetylacetonate/triphenylphosphine | 385 | 40-60 | 35-85 | 10-55 |
| | 1155 | 150 | 40 | 25 |
| | 3850 | 250 | 50 | 14 |
| Platinum(II) Iodide | 385 | 50-60 | 65 | 25-30 |
| | 1155 | 100 | 85 | 10 |
| | 3850 | 210 | 100 | 4 |
| Platinum(II) Iodide/4,5-Bis(diphenylphosphino)-9,9-dimethylxanthene | 385 | 10-20 | 70-85 | 2-8 |
| Platinum(II) Iodide/Oxydi-2,1-phenylenebis(diphenylphosphine) | 385 | 10 | 70 | 3 |
| Platinum(II) Iodide/triphenylphosphine | 385 | 0 | 100 | 1 |

Example 6

Example 1 was substantially repeated in several runs using the following conditions. Three different reaction temperatures were employed; 120° C., 140° C. and 160° C. Butyl benzoate was used as a solvent. Different amounts of benzoic acid were used in each of these runs as tabulated in Table 5 along with 500 ppm of para-benzoquinone. 2.5 milligrams of platinum homogeneous catalyst were used and 2.5 milligrams of the ligand were used. The resulting molar BA/metal ratios were as follows: ~122 for 100 mg of BA, ~280 for 230 mg of BA and ~440 for 360 mg of BA employed. Table 5 lists the results of these runs which includes TONs and yield of VB.

TABLE 5

| Catalyst/Ligand | Temp. (° C.) | TON | Yield of VB (%) |
|---|---|---|---|
| Benzoic Acid Used - 360 mg | | | |
| (1,5-Cyclooctadiene)dimethylplatinum(II) | 120 | 10 | 2 |
|  | 140 | 0 | 0 |
| Platinum acetylacetonate | 140 | 50 | 14 |
|  | 160 | 220 | 46 |
| Platinum acetylacetonate/ | 140 | 60 | 12 |
| triphenylphosphine | 160 | 175 | 37 |
| Benzoic Acid - 230 mg | | | |
| (1,5-Cyclooctadiene)dimethylplatinum(II) | 120 | 0 | 0 |
|  | 140 | 2 | 1 |
|  | 160 | 15 | 7 |
| Platinum acetylacetonate | 140 | 50-100 | 25-30 |
|  | 160 | 150-175 | 47-50 |
| Platinum acetylacetonate/ | 120 | 10 | 4 |
| triphenylphosphine | 140 | 20 | 9 |
|  | 160 | 70 | 20 |
| Benzoic Acid - 100 mg | | | |
| (1,5-Cyclooctadiene)dimethylplatinum(II) | 160 | 20 | 21 |
| Platinum acetylacetonate | 120 | 4 | 3 |
|  | 140 | 8 | 8 |
|  | 160 | 40 | 25 |
| Platinum acetylacetonate/triphenylphosphine | 120 | 5 | 3 |
|  | 140 | 10 | 8 |
|  | 160 | 60 | 41 |

Example 7

Example 1 was substantially repeated in several runs using the following conditions. Three different reaction temperatures were employed: 120° C., 140° C. and 160° C. Butyl benzoate was used as a solvent. The amount of benzoic acid used was 360 milligrams in combination with 500 ppm of para-benzoquinone and the appropriate amount of rhenium homogeneous catalyst was added so as to maintain a similar molar BA/metal ratio as in Example 1. Various ligands were also used with each of the rhenium metal complex as summarized in Table 6. Also summarized in Table 6 are the TONs, conversion and selectivity to VB.

TABLE 6

| Catalyst/Ligand | Temp. (° C.) | TON | Selectivity to VB (%) | Conv. (%) |
|---|---|---|---|---|
| Bromopentacarbonylrhenium(I) | 120 | 220 | 88 | 75 |
|  | 140 | 350 | 85 | 95 |
|  | 160 | 360 | 88 | 99 |
| Bromopentacarbonylrhenium(I)/4,5- | 120 | 50 | 85 | 20 |
| Bis(diphenylphosphino)-9,9- | 140 | 225 | 93 | 76 |
| dimethylxanthene | 160 | 315 | 90 | 100 |
| Bromopentacarbonylrhenium(I)/ | 120 | 70 | 85 | 30 |
| Oxydi-2,1-phenylenebis | 140 | 190 | 90 | 60 |
| (diphenylphosphine) | 160 | 200 | 85 | 78 |
| Bromopentacarbonylrhenium(I)/ | 120 | 65 | 92 | 20 |
| 1,2-DPPB | 140 | 130 | 80 | 45 |
|  | 160 | 110 | 60 | 60 |
| Dirhenium decacarbonyl | 120 | 20 | 100 | 7 |
|  | 140 | 350 | 90 | 90 |
|  | 160 | 180 | 92 | 100 |
| Dirhenium decacarbonyl/4,5-Bis | 120 | — | — | — |
| (diphenylphosphino)-9,9- | 140 | 325 | 95 | 100 |
| dimethylxanthene | 160 | 200 | 95 | 100 |
| Dirhenium decacarbonyl/Oxydi- | 120 | — | — | — |
| 2,1-phenylenebis | 140 | 77 | 85 | 40 |
| (diphenylphosphine) | 160 | 175 | 80 | 96 |
| Dirhenium decacarbonyl/1,2-DPPB | 120 | 0 | 18 | 1 |
|  | 140 | 42 | 71 | 20 |
|  | 160 | 170 | 48 | 95 |
| Pentacarbonylchlororhenium(I) | 120 | 200 | 90 | 80 |
|  | 140 | 320 | 93 | 100 |
|  | 160 | 360 | 90 | 100 |
| Pentacarbonylchlororhenium(I)/ | 120 | 12 | 100 | 1 |
| 4,5-Bis(diphenylphosphino)-9,9- | 140 | 80 | 100 | 20 |
| dimethylxanthene | 160 | 145 | 76 | 44 |
| Pentacarbonylchlororhenium(I)/ | 120 | 24 | 58 | 12 |
| Oxydi-2,1-phenylenebis | 140 | 50 | 80 | 19 |
| (diphenylphosphine) | 160 | 67 | 58 | 37 |
| Pentacarbonylchlororhenium(I)/ | 120 | 11 | 35 | 9 |
| 1,2-DPPB | 140 | 95 | 86 | 28 |
|  | 60 | 50 | 41 | 25 |

Example 8

Example 1 was substantially repeated in several runs using the following conditions. Three different reaction times were employed: 1 hour, 2 hours and 4 hours. Butyl benzoate was used as a solvent. All runs were carried out at a temperature of 140° C. The amount of benzoic acid used was 360 milligrams in combination with 500 ppm of para-benzoquinone and desired amount of rhenium homogeneous catalyst so as to maintain a similar molar BA/metal ratio as in Example 7. Various ligands were also used with each of the rhenium metal complex as summarized in Table 7. Also summarized in Table 7 are the TONs and percent yield of VB.

TABLE 7

| Catalyst/Ligand | Time (hr) | TON | Yield of VB (%) |
|---|---|---|---|
| Bromopentacarbonylrhenium(I) | 1 | 95 | 27 |
|  | 2 | 300 | 95 |
|  | 4 | 350 | 81 |
| Bromopentacarbonylrhenium(I)/4,5-Bis | 1 | 40 | 10 |
| (diphenylphosphino)-9,9-dimethylxanthene | 2 | 90 | 20 |
|  | 4 | 225 | 71 |
| Bromopentacarbonylrhenium(I)/Oxydi-2,1- | 1 | 17 | 4 |
| phenylenebis(diphenylphosphine) | 2 | 31 | 8 |
|  | 4 | 195 | 50 |
| Bromopentacarbonylrhenium(I)/1,2-DPPB | 1 | 16 | 3 |
|  | 2 | 70 | 18 |
|  | 4 | 120 | 37 |
| Dirhenium decacarbonyl | 1 | 32 | 10 |
|  | 2 | 190 | 99 |
|  | 4 | 350 | 85 |
| Dirhenium decacarbonyl/4,5-Bis | 1 | 0 | 0 |
| (diphenylphosphino)-9,9-dimethylxanthene | 2 | 0 | 0 |
|  | 4 | 320 | 95 |
| Dirhenium decacarbonyl/Oxydi-2,1- | 1 | — | — |
| phenylenebis(diphenylphosphine) | 2 | 0 | 0 |
|  | 4 | 90 | 35 |
| Dirhenium decacarbonyl/1,2-DPPB | 1 | 0 | 0 |
|  | 2 | 0 | 0 |
|  | 4 | — | — |
| Pentacarbonylchlororhenium(I) | 1 | 190 | 60 |
|  | 2 | 400 | 83 |
|  | 4 | 310 | 93 |
| Pentacarbonylchlororhenium(I)/4,5-Bis | 1 | 10 | 2.5 |
| (diphenylphosphino)-9,9-dimethylxanthene | 2 | 11 | 2 |
|  | 4 | — | — |
| Pentacarbonylchlororhenium(I)/Oxydi-2,1- | 1 | 0 | 0 |
| phenylenebis(diphenylphosphine) | 2 | 30 | 10 |
|  | 4 | 60 | 15 |
| Pentacarbonylchlororhenium(I)/1,2-DPPB | 1 | 0 | 0 |
|  | 2 | 20 | 5 |
|  | 4 | 95 | 26 |

Example 9

Example 1 was substantially repeated in several runs using the following conditions. The reaction temperature was maintained at 140° C. in all runs. Butyl benzoate was used as a solvent. The amount of benzoic acid used was 360 milligrams in combination with 500 ppm of para-benzoquinone. Appropriate amount of rhenium homogeneous catalyst was used to attain three different levels of molar BA/metal ratios of 385, 1150 and 3800. Various ligands were also used with each of the rhenium metal complex as summarized in Table 8 with these varied molar BA/metal ratio. Also summarized in Table 8 are the TONs, conversion and selectivity to VB.

TABLE 8

| Catalyst/Ligand | BA/metal ratio | TON | Selectivity to VB (%) | Conv. (%) |
|---|---|---|---|---|
| Bromopentacarbonylrhenium(I) | 385 | 347 | 80 | 100 |
|  | 1155 | 150 | 80 | 14 |
|  | 3850 | 30 | 0 | 0 |
| Bromopentacarbonylrhenium(I)/ 4,5-Bis(diphenylphosphino)-9,9-dimethylxanthene | 385 | 225 | 95 | 75 |
|  | 1155 | 380 | 98 | 33 |
|  | 3850 | 25 | 0 | 0 |
| Bromopentacarbonylrhenium(I)/ Oxydi-2,1-phenylenebis(diphenylphosphine) | 385 | 196 | 90 | 60 |
|  | 1155 | 350 | 100 | 30 |
|  | 3850 | 120 | — | 0 |
| Bromopentacarbonylrhenium(I)/ 1,2-DPPB | 385 | 140 | 80 | 45 |
|  | 1155 | 40 | 0 | 0 |
|  | 3850 | 25 | — | 0 |
| Dirhenium decacarbonyl | 385 | 350 | 90 | 92 |
|  | 1155 | 420 | 95 | 48 |
|  | 3850 | 148 | 100 | 0 |
| Dirhenium decacarbonyl/4,5-Bis(diphenylphosphino)-9,9-dimethylxanthene | 385 | 325 | 100 | 100 |
|  | 1155 | 115 | 100 | 8 |
|  | 3850 | 35 | 0 | 0 |
| Dirhenium decacarbonyl/Oxydi-2,1-phenylenebis(diphenylphosphine) | 385 | 80 | 80 | 40 |
|  | 1155 | 70 | 100 | 3 |
|  | 3850 | 25 | 0 | 0 |
| Dirhenium decacarbonyl/1,2-DPPB | 385 | 40 | — | 20 |
|  | 1155 | 95 | 100 | 5 |
|  | 3850 | 45 | 0 | 0 |
| Pentacarbonylchlororhenium(I) | 385 | 310 | 100 | 100 |
|  | 1155 | 320 | 95 | 38 |
|  | 3850 | 70 | — | 0 |
| Pentacarbonylchlororhenium(I)/ 4,5-Bis(diphenylphosphino)-9,9-dimethylxanthene | 385 | 90 | 100 | 20 |
|  | 1155 | 215 | 100 | 19 |
|  | 3850 | 50 | — | 0 |
| Pentacarbonylchlororhenium(I)/ Oxydi-2,1-phenylenebis(diphenylphosphine) | 385 | 50 | 80 | 20 |
|  | 1155 | 290 | 99 | 25 |
|  | 3850 | 75 | — | 0 |
| Pentacarbonylchlororhenium(I)/ 1,2-DPPB | 385 | 95 | 90 | 28 |
|  | 1155 | 20 | 0 | 0 |
|  | 3850 | 25 | 0 | 0 |

Example 10

Example 1 was substantially repeated in several runs using the following conditions. The reaction temperature was maintained at 120° C. in all runs. Butyl benzoate was used as a solvent. 2.5 milligrams of bromopentacarbonylrhenium(I) or pentacarbonylchlororhenium(I) and equimolar amount of various ligands as listed in Table 9 were used in these runs. Also summarized in Table 9 are the TONs and selectivity to VB.

TABLE 9

| Catalyst/Ligand or Additive | TON | Selectivity to VB (%) |
|---|---|---|
| Bromopentacarbonylrhenium(I)/Potassium Acetate | 210 | 95 |
| Bromopentacarbonylrhenium(I) | 180 | 90 |
| Bromopentacarbonylrhenium(I) (±)-2,2'-bis(diphenylphosphino)-1,1'-binaphthalene | 145 | 96 |
| Bromopentacarbonylrhenium(I)/tris(4-methoxyphenyl)-phosphine | 120 | 67 |
| Bromopentacarbonylrhenium(I)/1,1'-bis(diphenylphosphino)-ferrocene | 75 | 89 |
| Bromopentacarbonylrhenium(I)/1,2-DPPB | 60 | 90 |
| Bromopentacarbonylrhenium(I)/oxydi-2,1-phenylene-bis(diphenylphosphine) | 55 | 92 |
| Bromopentacarbonylrhenium(I)/4,5-bis(diphenylphosphino)-9,9-dimethylxanthene | 55 | 93 |
| Bromopentacarbonylrhenium(I)/tris(p-trifluoromethylphenyl)-phosphine | 33 | 75 |
| Bromopentacarbonylrhenium(I)/triphenylphosphine | 10 | 15 |
| Pentacarbonylchlororhenium(I) | 285-325 | 90-95 |
| Pentacarbonylchlororhenium(I)/sodium benzoate | 275 | 95 |
| Pentacarbonylchlororhenium(I)/potassium acetate | 225 | 94 |
| Pentacarbonylchlororhenium(I)/4,5-bis(diphenylphosphino)-9,9-dimethylxanthene | 120 | 90 |
| Pentacarbonylchlororhenium(I)/tris(p-trifluoromethylphenyl)phosphine | 60 | 84 |
| Pentacarbonylchlororhenium(I)/oxydi-2,1-phenylenebis-(diphenylphosphine) | 50 | 100 |
| Pentacarbonylchlororhenium(I)/tris(4-methoxyphenyl)-phosphine | 40 | 50 |
| Pentacarbonylchlororhenium(I)/(±)-2,2'-bis(diphenylphosphino)-1,1'-binaphthalene | 50 | 98 |
| Pentacarbonylchlororhenium(I)/1,1'-bis(diphenylphosphino)-ferrocene | 43 | 80 |
| Pentacarbonylchlororhenium(I)/1,2-DPPB | 11 | 33 |
| Pentacarbonylchlororhenium(I)/triphenylphosphine | 25 | 35 |

Example 11

Example 1 was substantially repeated in several runs using the following conditions. The reaction temperature was maintained at 140° C. in all runs. Butyl benzoate was used as a solvent. Benzoic acid was used in an amount of 360 mg in combination with 2.5 milligrams of pentacarbonylchlororhenium(I) or dirhenium decacarbonyl and an equimolar amount of various ligands as listed in Table 10. Also summarized in Table 10 are the TONs and selectivity to VB.

TABLE 10

| Catalyst/Ligand or Additive | TON | Selectivity to VB (%) |
|---|---|---|
| Pentacarbonylchlororhenium(I) | 400 | 97 |
| Pentacarbonylchlororhenium(I)/4,5-bis(diphenylphosphino)-9,9-dimethylxanthene | 200 | 95 |
| Pentacarbonylchlororhenium(I)/1,2-DPPB | 145 | 76 |
| Pentacarbonylchlororhenium(I)/triphenylphosphine | 35 | 27 |
| Dirhenium decacarbonyl | 380 | 96 |
| Dirhenium decacarbonyl/tris(4-methoxyphenyl)phosphine | 325 | 94 |
| Dirhenium decacarbonyl/potassium acetate | 150 | 92 |
| Dirhenium decacarbonyl/triphenylphosphine | 120 | 55 |
| Dirhenium decacarbonyl/4,5-bis(diphenylphosphino)-9,9-dimethylxanthene | 115 | 94 |
| Dirhenium decacarbonyl/oxydi-2,1-phenylenebis(diphenylphosphine) | 90 | 86 |
| Dirhenium decacarbonyl/sodium benzoate | 80 | 93 |
| Dirhenium decacarbonyl/tris(p-trifluoromethylphenyl)phosphine | 80 | 84 |

Example 12

Example 1 was substantially repeated in several runs using the following conditions. In each of the runs, at least one of the following reaction temperature was maintained: 50° C. (in acetonitrile as a solvent), 80° C. or 90° C. (in toluene as a solvent) or 120° C. (in butyl benzoate as a solvent). In all cases the amount of benzoic acid used was 100 milligrams in combination with 500 ppm of para-benzoquinone and 10 milligrams of rhodium homogeneous catalyst. The observed results of TON and yield of VB are summarized in Table 11.

TABLE 11

| Catalyst | Temp (° C.) | TON | Yield of VB (%) |
|---|---|---|---|
| (Acetylacetonato)dicarbonylrhodium(I) | 50 | 0 | <1 |
|  | 80 | 2 | 9 |
|  | 90 | 2.5 | 11 |
| 1,1'-Bis(diisopropylphosphino)-ferrocene(cod)Rh-phosphotungstic acid | 80 | 0 | 0 |
| Bis(1,5-cyclooctadiene)-dirhodium(I)dichloride | 50 | 0 | 0 |
|  | 120 | 5 | 23 |
| Dichloro(pentamethyl-cyclopentadienyl)rhodium(III) dimer | 50 | 0.2 | <1 |
|  | 80 | 1 | 4 |
|  | 90 | 2.8 | 5 |
| Methoxy(cyclooctadiene)rhodium(I) dimer | 50 | 0.25 | 1 |
|  | 80 | 4 | 20 |

Example 13

Example 1 was substantially repeated in several runs using the following conditions. The reaction temperature was maintained at 120° C. in butyl benzoate as a solvent in all of the runs. The amount of benzoic acid used was either 100 milligrams or 360 milligrams in combination with 500 ppm of para-benzoquinone. The catalyst used was rhodium (II) acetate dimer. The amount of catalyst used was 2.5 milligrams with 360 milligrams of benzoic acid or 10 milligrams of catalyst with 100 milligrams of benzoic acid. Various ligands were used with the rhodium catalyst at ligand/metal ratio of one. The observed results of TON and yield of VB are summarized in Table 12.

TABLE 12

| Ligand | Amount of Cat/BA | TON | Yield of VB (%) |
|---|---|---|---|
| None | 2.5/360 | 0 | 0 |
|  | 10/100 | 0 | 0 |
| 1,1'-Bis(diphenylphosphino)-ferrocene | 2.5/360 | 22 | 9 |
|  | 10/100 | 10 | 59 |
| 1,2-DPPB | 2.5/360 | 30-45 | 12-16 |
|  | 10/100 | 8 | 61 |
| 4,5-Bis(diphenylphosphino)-9,9-dimethylxanthene | 2.5/360 | 26 | 9 |
|  | 10/100 | 7 | 39 |
| Diphenyl-2-pyridylphosphine | 2.5/360 | 42 | 18 |
|  | 10/100 | 11 | 54 |
| Oxydi-2,1-phenylenebis-(diphenylphosphine) | 2.5/360 | 60 | 22 |
|  | 10/100 | 12 | 55 |
| Tris(p-trifluoromethylphenyl)phosphine | 2.5/360 | 6 | 2 |
|  | 10/100 | 3 | 17 |
| Triphenylphosphine | 2.5/360 | 20 | 7 |
|  | 10/100 | 8 | 55 |
| Tris(1-naphthyl)phosphine | 2.5/360 | 18 | 6 |
|  | 10/100 | 10 | 54 |
| Tris(2,4,6-trimethoxyphenyl)-phosphine | 2.5/360 | 6 | 2.5 |
|  | 10/100 | 8 | 42 |
| Tris(4-methoxyphenyl)-phosphine | 2.5/360 | 5 | 2 |
|  | 10/100 | 5 | 27 |

Example 14

Example 1 was substantially repeated in several runs using the following conditions. In each of the runs at least one of the following temperatures and solvents were employed: 50° C. (acetonitrile), 80° C. (toluene) or 90° C. (toluene). The amount of benzoic acid used was 100 milligrams in combination with 500 ppm of para-benzoquinone and 10 milligrams of ruthenium catalyst. Various ligands were also used with each of the ruthenium metal complex as summarized in Table 13. Also summarized in Table 13 are the TONs, conversion and selectivity to VB.

TABLE 13

| Catalyst/Ligand | Temp. (° C.) | TON | Selectivity to VB (%) | Conv. (%) |
|---|---|---|---|---|
| bis(2-methylallyl)(1,5-cyclooctadiene)-ruthenium(II)/1,2-DPPB | 50 | 10 | 75 | 55 |
|  | 80 | 4 | 27 | 50 |
| triruthenium dodecacarbonyl/triphenylphosphine | 50 | 0.1 | 5 | 12 |
|  | 80 | 6 | 37 | 80 |
|  | 90 | 4 | 25 | 95 |
| triruthenium dodecacarbonyl | 50 | 0 | 0-8 | 10 |
|  | 80 | 0.4-1 | 7-15 | 10-45 |
| dichloro(p-cymene)tricyclohexylphosphine-ruthenium(II) | 50 | 0 | 1 | 10 |
|  | 80 | 2.5 | 25 | 20 |
| tricarbonyldichlororuthenium(II) dimer | 80 | 0.5 | 5 | 42 |
| Chloro(pentamethylcyclopentadienyl)ruthenium(II) tetramer | 50 | 0 | 2 | 8 |
|  | 80 | 0 | 3 | 31 |

Example 15

Example 1 was substantially repeated in several runs using the following conditions. In each of the runs at least one of the following temperatures was employed: 120° C. or 160° C. Butyl benzoate was used as a solvent. The amount of benzoic acid used was 360 milligrams in combination with 500 ppm of para-benzoquinone and the necessary amount of ruthenium catalyst to maintain a similar acid/metal molar ratio to that of Example 1. Various ligands were also used with each of the ruthenium metal complexes with a ligand/metal molar ratio of one as summarized in Table 14. Also summarized in Table 14 are the TONs and yield of VB.

TABLE 14

| Catalyst/Ligand | Temp. (° C.) | TON | Yield of VB (%) |
|---|---|---|---|
| triruthenium dodecacarbonyl/1,2-DPPB | 120 | 35 | 12 |
|  | 160 | 105 | 28 |
| triruthenium dodecacarbonyl/triphenylphosphine | 120 | 25 | 6 |
|  | 160 | 165 | 60 |
| triruthenium dodecacarbonyl | 120 | 5 | 4 |
|  | 160 | 5 | 1 |
| bis(2-methylallyl)(1,5-cyclooctadiene)ruthenium(II)/1,2-DPPB | 120 | 20 | 6 |
|  | 160 | 18 | 4 |
| bis(2-methylallyl)(1,5-cyclooctadiene)ruthenium(II)/triphenylphosphine | 120 | 10 | 5 |
|  | 160 | 7 | 3 |
| bis(2-methylallyl)(1,5-cyclooctadiene)ruthenium(II) | 120 | 5 | 3 |
|  | 160 | 0 | 0 |

Example 16

Example 1 was substantially repeated in several runs using the following conditions. The reaction temperature was maintained at 120° C. Butyl benzoate or mesitylene was used as a solvent. The amount of benzoic acid used was 360 milligrams in combination with 500 ppm of para-benzoquinone and 10 milligrams of triruthenium dodecacarbonyl as a catalyst. In each of these runs, various ligands were used with a constant ligand/metal ratio of one. The observed results of TON and yield of VB are summarized in Table 15 wherein butyl benzoate was used as the solvent and Table 16 summarizes similar results obtained for mesitylene.

TABLE 15

Results for Butyl Benzoate as a Solvent

| Ligand | TON | Yield of VB (%) |
|---|---|---|
| (+)-2,2'-Bis-(diphenylphosphino)-1,1'-binapthalene | 0.2 | 0.5 |
| 1,1'-Bis(diphenylphosphino)ferrocene | 0.5 | 1 |
| 1,2-DPPB | — | — |
| 4,5-Bis(diphenylphosphino)-9,9-dimethylxanthene | 0 | 0 |
| Diphenyl-2-pyridylphosphine | 1.4 | 2.5 |
| Oxydi-2,1-phenylenebis(diphenylphosphine) | 0.25 | 0.5 |
| Triphenylphosphine | 2.7 | 4 |
| Tris(1-naphthyl)phosphine | 1.2 | 3 |
| Tris(2,4,6-trimethoxyphenyl)phosphine | 0.6 | 1.5 |
| Tris(4-methoxyphenyl)phosphine | 3.4 | 6 |
| Tris(p-trifluoromethylphenyl)phosphine | 1.4 | 3 |
| None | 0.4 | 1 |

TABLE 16

Results for Mesitylene as a Solvent

| Ligand | TON | Yield of VB (%) |
|---|---|---|
| (+)-2,2'-Bis-(diphenylphosphino)-1,1'-binapthalene | — | — |
| 1,1'-Bis(diphenylphosphino)ferrocene | 0.6 | 2 |
| 1,2-DPPB | 1.8 | 3 |
| 4,5-Bis(diphenylphosphino)-9,9-dimethylxanthene | 0 | 0 |
| Diphenyl-2-pyridylphosphine | 0.9 | 2 |
| Oxydi-2,1-phenylenebis(diphenylphosphine) | — | — |
| Triphenylphosphine | 1.7 | 3 |
| Tris(1-naphthyl)phosphine | 2.0 | 3 |
| Tris(2,4,6-trimethoxyphenyl)phosphine | 0.5 | 1 |
| Tris(4-methoxyphenyl)phosphine | 3.4 | 6 |
| Tris(p-trifluoromethylphenyl)phosphine | 1.75 | 3 |
| None | 0.4 | 1 |

Example 17

Example 1 was substantially repeated in several runs using the following conditions. The reaction temperatures were maintained respectively at 50° C. (in acetonitrile as a solvent), 80° C. (in toluene as a solvent) and 120° C. (in butyl benzoate as a solvent). In all cases the amount of benzoic acid used was 360 milligrams in combination with 500 ppm of para-benzoquinone and 10 milligrams of bis(2-methylallyl)(1,5-cyclooctadiene)ruthenium(II) as a catalyst. In each of these runs, various ligands were used with a constant ligand/metal ratio of one. The observed results of TON, conversion and selectivity to VB are summarized in Table 17.

TABLE 17

| Ligand | Temp (° C.) | TON | Selectivity to VB (%) | Conv. (%) |
|---|---|---|---|---|
| (+)-2,2'-Bis-(diphenylphosphino)-1,1'-binapthalene | 50 | 0 | 0 | 9 |
|  | 80 | 2.5 | 18 | 15 |
|  | 120 | 2.0 | 13 | 15 |
| 1,1'-Bis(diphenylphosphino)ferrocene | 50 | 0.5 | 10 | 10 |
|  | 120 | 4.0 | 40 | 11 |
| 1,2-DPPB | 50 | 2 | 25 | 9 |
|  | 80 | 4 | 25 | 11 |
|  | 120 | 3.5 | 50 | 10 |
| 4,5-Bis(diphenylphosphino)-9,9-dimethylxanthene | 50 | 0 | 0 | 8 |
|  | 80 | 0 | 10 | 5 |
|  | 120 | 0 | 2 | 10 |
| Diphenyl-2-pyridylphosphine | 50 | 0 | 0 | 5 |
|  | 80 | 7 | 25 | 30 |
|  | 120 | 1 | 50 | 4 |
| Oxydi-2,1-phenylenebis(diphenylphosphine) | 50 | 0 | 0 | 9 |
|  | 120 | 1 | 10 | 11 |
| Triphenylphosphine | 80 | 6 | 20 | 30 |
|  | 120 | 2.4 | 90 | 3 |
| Tris(1-naphthyl)phosphine | 50 | 0 | 0 | 10 |
|  | 80 | 2.3 | 15 | 20 |
|  | 120 | 2.5 | — | 0 |
| Tris(2,4,6-trimethoxyphenyl)phosphine | 50 | 0 | 0 | 5 |
|  | 80 | 0.5 | 20 | 2 |
|  | 120 | 0.5 | 0 | 0 |
| Tris(4-methoxyphenyl)phosphine | 50 | 0 | 0 | 4 |
|  | 80 | 11 | 50 | 20 |
|  | 120 | 2.5 | 20 | 15 |
| Tris(p-trifluoromethylphenyl)phosphine | 50 | 0 | 0 | 10 |
|  | 80 | 7 | 18 | 38 |
|  | 120 | 3 | 21 | 15 |
| None | 50 | 0 | 0 | 5 |
|  | 80 | 2 | 5 | 22 |
|  | 120 | 1 | 5 | 9 |

Example 18

Example 1 was substantially repeated in several runs using the following conditions. The reaction temperatures were maintained either at 80° C. (in toluene as a solvent) or at 120° C. (in butyl benzoate as a solvent). In all cases the amount of benzoic acid used was 230 milligrams in combination with 500 ppm of para-benzoquinone and 10 milligrams of palladium acetate as a catalyst. In each of these runs, various ligands were used with a constant molar ligand/metal ratio of 0.5. The observed results of TON, conversion and selectivity to VB are summarized in Table 18.

TABLE 18

| Ligand | Temp (° C.) | TON | Selectivity to VB (%) | Conv. (%) |
|---|---|---|---|---|
| (+)-2,2'-(diphenylphosphino)-1,1'-binapthalene | 80 | 4 | 54 | 21 |
|  | 120 | 24 | 68 | 74 |
| 1,1'-Bis(diphenylphosphino)ferrocene | 80 | 4.5 | 26 | 31 |
|  | 120 | 16 | 74 | 50 |
| 1,2-DPPB | 80 | 3 | 44 | 18 |
|  | 120 | 8 | 58 | 44 |
| 4,5-Bis(diphenylphosphino)-9,9-dimethylxanthene | 80 | 8 | 63 | 33 |
|  | 120 | 19 | 75 | 60 |
| Diphenyl-2-pyridylphosphine | 80 | 4 | 70 | 15 |
|  | 120 | 12 | 62 | 42 |
| Oxydi-2,1-phenylenebis(diphenylphosphine) | 80 | 4 | 49 | 22 |
|  | 120 | 5 | 60 | 30 |
| Triphenylphosphine | 80 | 2.5 | 100 | 5 |
|  | 120 | 7 | 73 | 18 |
| Tris(1-naphthyl)phosphine | 80 | 2 | 60 | 8 |
|  | 120 | 11 | 77 | 35 |
| Tris(2,4,6-trimethoxyphenyl)phosphine | 80 | 2 | 58 | 5 |
|  | 120 | 2 | 59 | 8 |
| Tris(4-methoxyphenyl)phosphine | 80 | 3 | 45 | 20 |
|  | 120 | 3 | 62 | 14 |
| Tris(p-trifluoromethylphenyl)phosphine | 80 | 2 | 60 | 8 |
|  | 120 | 7 | 72 | 20 |
| None | 80 | 2 | 41 | 6 |
|  | 120 | 2 | 30 | 12 |

Example 19

Example 1 was substantially repeated in several runs using the following conditions. The reaction temperatures were maintained either at 80° C. (in toluene as a solvent) or at 120° C. (in butyl benzoate as a solvent). The amount of benzoic acid used was 230 milligrams in combination with 500 ppm of para-benzoquinone in all runs, and 10 milligrams of palladium acetate was used as a catalyst. In each of these runs, various ligands were used with a constant molar ligand/metal ratio of 1.0. The observed results of TON, conversion and yield of VB are summarized in Table 19.

TABLE 19

| Ligand | Temp (° C.) | TON | Yield of VB (%) |
|---|---|---|---|
| 1,2-DPPB | 120 | 5 | 13 |
| Diphenyl-2-pyridylphosphine | 120 | 19 | 50 |
| Oxydi-2,1-phenylenebis(diphenylphosphine) | 120 | 12 | 28 |
| Triphenylphosphine | 120 | 6 | 12 |
| Tris(1-naphthyl)phosphine | 120 | 18 | 44 |
| Tris(2,4,6-trimethoxyphenyl)phosphine | 120 | 4 | 14 |
| Tris(4-methoxyphenyl)phosphine | 120 | 3 | 12 |
| Tris(p-trifluoromethylphenyl)phosphine | 120 | 7 | 15 |
| None | 80 | 1.5 | 4 |
|  | 120 | 2 | 5 |

Example 20

Example 1 was substantially repeated in several runs using the following conditions. The reaction temperatures were maintained either at 120° C. or at 160° C. Butyl benzoate was used as a solvent in all runs. The amount of benzoic acid used was 360 milligrams in combination with 500 ppm of para-benzoquinone in all runs, and an appropriate amount of palladium acetate was used as a catalyst to result in a molar BA/metal ratio in the range of about 235-441. In each of these runs, various ligands were used with a variable molar ligand/metal ratio of 0.6 to 1.0. The observed results of TON and yield of VB are summarized in Table 20.

TABLE 20

| Ligand | Temp (° C.) | TON | Yield of VB (%) |
|---|---|---|---|
| 1,1'-Bis(diphenylphosphino)ferrocene | 160 | 12 | 4.4 |
| 1,2-DPPB | 160 | 145 | 53 |
| 4,5-Bis(diphenylphosphino)-9,9-dimethylkxanthene | 160 | 13 | 4 |
| Diphenyl-2-pyridylphosphine | 160 | 5 | 2.3 |
| Oxydi-2,1-phenylenebis(diphenylphosphine) | 160 | 10 | 3 |
| Tris(1-naphthyl)phosphine | 120 | 19 | 5 |
|  | 160 | 43 | 12 |
| None | 160 | 0 | 0 |

Example 21

Example 1 was substantially repeated in several runs using the following conditions. The reactions were carried out at various temperatures in different solvents as follows: 50° C. in acetonitrile, 80° C. in toluene, 120° C. and 160° C. in butyl benzoate. The amount of benzoic acid used was 100 milligrams in combination with 500 ppm of para-benzoquinone in all runs, and 10 milligrams of iridium complex catalyst except for runs in the presence of iridium(IV) oxide, in which case 2.5 milligrams of catalyst was used. The observed results of TON, conversion and selectivity to VB are summarized in Table 21.

TABLE 21

| Catalyst | Temp (° C.) | TON | Selectivity to VB (%) | Conv. (%) |
|---|---|---|---|---|
| (1,5-Cyclooctadiene)-hexafluoroacetylacetonato)iridium(I) | 120 | 18 | 52 | 85 |
|  | 160 | 17.5 | 38 | 98 |
| Bis(1,5-cyclooctadiene)diiridium(I) dichloride | 50 | 0 | 6 | 8 |
|  | 80 | 2 | 23 | 25 |
|  | 120 | 6 | 28 | 75 |
|  | 160 | 2.5 | 11 | 70 |
| Bis(1,5-cyclooctadiene)iridium(I) tetrafluoroborate | 50 | 0 | 2 | 4 |
|  | 80 | 2 | 22 | 20 |
|  | 120 | 7.5 | 40 | 44 |
|  | 160 | 1 | 5 | 42 |
| Ir(III) acetylacetonate | 50 | 0 | 0 | 4 |
|  | 80 | 0 | 0 | 8 |
|  | 120 | 0 | 5 | 8 |
|  | 160 | 1 | 15 | 22 |
| Ir(IV) oxide | 120 | 0 | 0 | 8 |
|  | 160 | 0 | 2 | 14 |

Example 22

Example 1 was substantially repeated in several runs using the following conditions. The reactions were carried out at two temperatures, 120° C. and 160° C., in butyl benzoate as a solvent. In all runs, the amount of benzoic acid used was 360 milligrams in combination with 500 ppm of para-benzoquinone. An appropriate amount of iridium homogeneous catalyst was used so as to obtain a constant molar BA/metal ratio of 385. The observed results of TON, conversion and selectivity to VB are summarized in Table 18.

TABLE 22

| Catalyst | Temp (° C.) | TON | Selectivity to VB (%) | Conv. (%) |
|---|---|---|---|---|
| (1,5-Cyclooctadiene)(methoxy)iridium(I) dimer | 120 | 30 | 65 | 10 |
|  | 160 | 5 | 6 | 17.5 |
| (1,5-cyclooctadiene)-5-indenyliridium(I) | 120 | 30 | 66 | 11 |
|  | 160 | 6 | 8 | 19 |
| (Acetylacetonato)(1,5-cyclooctadiene)iridium(I) | 120 | 55 | 52 | 35 |
|  | 160 | 38 | 20 | 47 |
| (1,5-cyclooctadiene)(hexafluoroacetylacetonato)-iridium(I) | 120 | 29 | 69 | 12 |
|  | 160 | 6 | 10 | 23 |
| Bis(1,5-cyclooctadiene)diiridium(I) dichloride | 120 | 18-28 | 40-56 | 10-22 |
|  | 160 | 9 | 8 | 28 |
| Bis(1,5-cyclooctadiene)iridium(I) tetrafluoroborate | 120 | 8 | 82 | 4 |
|  | 160 | 5 | 5 | 22 |

Example 23

Example 1 was substantially repeated in several runs using the following conditions. The reactions were carried out at two temperatures, 120° C. and 160° C., in butyl benzoate as a solvent. In all runs the amount of benzoic acid used was 100 milligrams in combination with 500 ppm of para-benzoquinone and 10 milligrams of iridium homogeneous catalyst. Triphenylphosphine or 1,2-DPPB were used as a ligand with various iridium metal complex catalysts at a metal/ligand molar ratio of one. The observed results of TON, conversion and selectivity to VB are summarized in Table 23.

TABLE 23

| Catalyst/Ligand | Temp (° C.) | TON | Selectivity to VB (%) | Conv. (%) |
|---|---|---|---|---|
| (1,5-cyclooctadiene)- (hexafluoroacetylacetonato)-iridium(I) | 120 | 18 | 50 | 85 |
|  | 160 | 17.5 | 38 | 95 |
| (1,5-cyclooctadiene)- (hexafluoroacetylacetonato)- iridium(I)/1,2-DPPB | 120 | 2 | 18 | 20 |
|  | 160 | 5 | 20 | 48 |
| (1,5-cyclooctadiene)- (hexafluoroacetylacetonato)- iridium(I)/Triphenylphosphine | 120 | 4 | 18 | 44 |
|  | 160 | 10 | 28 | 90 |
| Bis(1,5-cyclooctadiene)diiridium(I) dichloride | 120 | 6 | 28 | 78 |
|  | 160 | 2 | 10 | 68 |
| Bis(1,5-cyclooctadiene)diiridium(I) dichloride/1,2-DPPB | 120 | 4 | 30 | 66 |
|  | 160 | 3 | 18 | 65 |
| Bis(1,5-cyclooctadiene)diiridium(I) dichloride/Triphenylphosphine | 120 | 2.5 | 20 | 40 |
|  | 160 | 2.5 | 12 | 63 |
| Bis(1,5-cyclooctadiene)iridium(I) tetrafluoroborate | 120 | 7.5 | 40 | 43 |
|  | 160 | 1 | 5 | 41 |
| Bis(1,5-cyclooctadiene)iridium(I) tetrafluoroborate/Triphenylphosphine | 120 | 4.5 | 25 | 42 |
|  | 160 | 3 | 13 | 55 |
| Ir(III) Acetylacetonate | 120 | 0 | 5 | 9 |
|  | 160 | 2 | 15 | 20 |
| Ir(III) Acetylacetonate/1,2-DPPB | 120 | 0 | 0 | 5 |
|  | 160 | 0 | 0 | 6 |
| Ir(III) Acetylacetonate/ Triphenylphosphine | 120 | 0 | 0 | 3 |
|  | 160 | 0 | 3 | 7 |

Example 24

A suitable reactor vessel equipped with appropriate inlets and stirring device is charged with 100 milligrams of 2-ethylhexanoic acid and 500 ppm of para-benzoquinone. The reactor is purged two to three times with nitrogen and a constant flow of nitrogen is maintained. To this mixture is added 900 milligrams of butyl benzoate with stirring and the mixture is heated slightly if necessary to dissolve 2-ethylhexanoic acid. To this solution is added 10 milligrams of platinum acetylacetonate with stirring and the entire mixture is heated to 140° C. At this time, acetylene is fed into the reactor at a steady stream maintaining the pressure of acetylene at 1.7 bars. The reaction mixture is stirred for an additional 4 hours. At the end of this period, a sample of the reaction mixture is removed and analyzed by GC as described above.

Example 25

Example 24 is substantially repeated in several runs using the following conditions. The reaction temperature is maintained at either 120° C. or 160° C. Butyl benzoate is used as a solvent. The amount of 2-ethylhexanoic acid used is 100 milligrams in combination with 500 ppm of para-benzoquinone and 10 milligrams of platinum homogeneous catalyst. Various platinum catalysts that can be used in this Example are summarized in Table 24.

TABLE 24

| Catalyst | Temp. (° C.) |
|---|---|
| (1,5-Cyclooctadiene)dimethylplatinum(II) | 120 |
|  | 160 |
| Platinum acetylacetonate | 120 |
|  | 160 |
| Platinum(II) bromide | 120 |
|  | 160 |
| Platinum(II) chloride | 120 |
|  | 160 |
| Platinum(IV) chloride | 120 |
|  | 160 |
| Platinum(II) iodide | 120 |
|  | 160 |

Example 26

Example 24 is substantially repeated in several runs using the following conditions. Three different reaction temperatures are employed: 120° C., 140° C. and 160° C. Butyl benzoate is used as a solvent. The amount of 2-ethylhexanoic acid used is 360 milligrams in combination with 500 ppm of para-benzoquinone and desired amount of platinum homogeneous catalyst so as to maintain similar molar 2EHA/metal ratio as in Example 24 or 25. Various ligands are also used with each of the platinum metal complex as summarized in Table 25.

TABLE 25

| Catalyst/Ligand |
|---|
| (1,5-Cyclooctadiene)dimethylplatinum(II) |
| (1,5-Cyclooctadiene)dimethylplatinum(II)/ 4,5-Bis(diphenylphosphino)-9,9-dimethylxanthene |
| (1,5-Cyclooctadiene)dimethylplatinum(II)/ Oxydi-2,1-phenylenebis(diphenylphosphine) |
| (1,5-Cyclooctadiene)dimethyl-platinum(II)/ triphenylphosphine |
| Platinum acetylacetonate |
| Platinum acetylacetonate/ 4,5-Bis(diphenylphosphino)-9,9-dimethylxanthene |
| Platinum acetylacetonate/ Oxydi-2,1-phenylenebis(diphenylphosphine) |
| Platinum acetylacetonate/triphenylphosphine |
| Platinum(II) iodide |
| Platinum(II) iodide/ 4,5-Bis(diphenylphosphino)-9,9-dimethylxanthene |
| Platinum(II) iodide/ Oxydi-2,1-phenylenebis(diphenylphosphine) |
| Platinum(II) iodide/triphenylphosphine |

Example 27

Example 24 is substantially repeated in several runs using the following conditions. In all runs the reaction temperature is maintained at 140° C. Butyl benzoate is used as a solvent. The amount of 2-ethylhexanoic acid used is 360 milligrams in combination with 500 ppm of para-benzoquinone. Desired amount of platinum homogeneous catalyst is used to attain three different levels of molar 2EHA/metal ratios of 385, 1155 and 3850. Various ligands are also used with each of the platinum metal complex as summarized in Table 26 with these varied molar 2EHA/metal ratio.

TABLE 26

| Catalyst/Ligand | 2EHA/metal ratio |
|---|---|
| (1,5-Cyclooctadiene)dimethylplatinum(II) | 385 |
|  | 1155 |
|  | 3850 |
| (1,5-Cyclooctadiene)dimethylplatinum(II)/4,5- Bis(diphenylphosphino)-9,9-dimethylxanthene | 385 |
|  | 1155 |
|  | 3850 |

TABLE 26-continued

| Catalyst/Ligand | 2EHA/metal ratio |
|---|---|
| (1,5-Cyclooctadiene)dimethylplatinum(II)/Oxydi-2,1-phenylenebis(diphenylphosphine) | 385<br>1155<br>3850 |
| (1,5-Cyclooctadiene)dimethyl-platinum(II)/triphenylphosphine | 385<br>1155<br>3850 |
| Platinum acetylacetonate | 385<br>1155<br>3850 |
| Platinum acetylacetonate/4,5-Bis(diphenylphosphino)-9,9-dimethylxanthene | 385<br>1155<br>3850 |
| Platinum acetylacetonate/Oxydi-2,1-phenylenebis(diphenylphosphine) | 385<br>1155<br>3850 |
| Platinum acetylacetonate/triphenylphosphine | 385<br>1155<br>3850 |

Example 28

Example 24 is substantially repeated in several runs using the following conditions. Three different reaction temperatures are employed: 120° C., 140° C. and 160° C. Butyl benzoate is used as a solvent. The amount of 2-ethylhexanoic acid used is 360 milligrams in combination with 500 ppm of para-benzoquinone and desired amount of rhenium homogeneous catalyst so as to maintain similar molar 2EHA/metal ratio as in Example 24 or 25. Various ligands are also used with each of the rhenium metal complex as summarized in Table 27.

TABLE 27

| Catalyst/Ligand |
|---|
| Bromopentacarbonylrhenium(I) |
| Bromopentacarbonylrhenium(I)/<br>4,5-Bis(diphenylphosphino)-9,9-dimethylxanthene |
| Bromopentacarbonylrhenium(I)/<br>Oxydi-2,1-phenylenebis(diphenylphosphine) |
| Bromopentacarbonylrhenium(I)/1,2-DPPB |
| Dirhenium decacarbonyl |
| Dirhenium decacarbonyl/<br>4,5-Bis(diphenylphosphino)-9,9-dimethylxanthene |
| Dirhenium decacarbonyl/<br>Oxydi-2,1-phenylenebis(diphenylphosphine) |
| Dirhenium decacarbonyl/1,2-DPPB |
| Pentacarbonylchlororhenium(I) |
| Pentacarbonylchlororhenium(I)/4,5-Bis(diphenylphosphino)-9,9-dimethylxanthene |
| Pentacarbonylchlororhenium(I)/<br>Oxydi-2,1-phenylenebis(diphenylphosphine) |
| Pentacarbonylchlororhenium(I)/1,2-DPPB |

Example 29

Example 24 is substantially repeated in several runs using the following conditions. The reaction temperatures are maintained either at 50° C. (in acetonitrile as a solvent), 80° C. or 90° C. (in toluene as a solvent) or 120° C. (in butyl benzoate as a solvent). In all cases the amount of 2-ethylhexanoic acid used is 100 milligrams in combination with 500 ppm of para-benzoquinone and 10 milligrams of rhodium homogeneous catalyst. Various rhodium catalysts used are summarized in Table 28.

TABLE 28

| Rhodium Catalysts |
|---|
| (Acetylacetonato)dicarbonylrhodium(I) |
| 1,1'-Bis(diisopropylphosphino)-ferrocene(cod)Rh-phosphotungstic acid |
| Bis(1,5-cyclooctadiene)-dirhodium(I)dichloride |
| Dichloro(pentamethylcyclopentadienyl)rhodium(III) dimer |
| Methoxy(cyclooctadiene)rhodium(I) dimer |

Example 30

Example 24 is substantially repeated in several runs using the following conditions. In all runs the reaction temperatures is maintained at 120° C. in butyl benzoate as a solvent. The amount of 2-ethylhexanoic acid used is either 100 milligrams with 10 mg of catalyst complex or 360 milligrams with 25 mg of catalyst complex in combination with 500 ppm of para-benzoquinone. The catalyst used is rhodium(II) acetate dimer. The amount of catalyst used is 2.5 milligrams with 100 milligrams of 2-ethylhexanoic acid or 10 milligrams of catalyst with 360 milligrams of 2-ethylhexanoic acid. Various ligands are used with the rhodium catalyst at ligand/metal ratio of one and are summarized in Table 29.

TABLE 29

| Ligand |
|---|
| 1,1'-Bis(diphenylphosphino)-ferrocene |
| 1,2-DPPB |
| 4,5-Bis(diphenylphosphino)-9,9-dimethylxanthene |
| Diphenyl-2-pyridylphosphine |
| Oxydi-2,1-phenylenebis-(diphenylphosphine) |
| Tris(p-trifluoromethylphenyl)phosphine |
| Triphenylphosphine |
| Tris(1-naphthyl)phosphine |
| Tris(2,4,6-trimethoxyphenyl)-phosphine |
| Tris(4-methoxyphenyl)-phosphine |

Example 31

Example 24 is substantially repeated in several runs using the following conditions. The reaction temperatures are maintained either at 50° C. (in acetonitrile as a solvent), 80° C. or 90° C. (in toluene as a solvent) or 120° C. (in butyl benzoate as a solvent). In all cases the amount of 2-ethylhexanoic acid used is 100 milligrams in combination with 500 ppm of para-benzoquinone and 10 milligrams of ruthenium homogeneous catalyst. Various ruthenium catalysts and ligands used are summarized in Table 30.

TABLE 30

| Ruthenium Catalyst/Ligand |
|---|
| Bis(2-methylallyl)(1,5-cyclooctadiene)-ruthenium(II)/1,2-DPPB |
| Triruthenium dodecacarbonyl/Triphenylphosphine |
| Triruthenium dodecacarbonyl |
| Dichloro(p-cymene)tricyclohexylphosphine-ruthenium(II) |
| Tricarbonyldichlororuthenium(II) dimer |
| Triruthenium dodecacarbonyl/1,2-DPPB |
| Bis(2-methylallyl)(1,5-cyclooctadiene)ruthenium(II)/Triphenylphosphine |

Example 32

Example 24 is substantially repeated in several runs using the following conditions. The reaction temperatures are maintained either at 80° C. (in toluene as a solvent) or at 120° C. (in butyl benzoate as a solvent). In all cases the amount of 2-ethylhexanoic acid used is 230 milligrams in combination with 500 ppm of para-benzoquinone and 10 milligrams of palladium acetate as a catalyst. In each of these runs, various ligands are used with a constant molar ligand/metal ratio of 1.0 and are summarized in Table 31.

TABLE 31

Ligand 1,2-DPPB
Diphenyl-2-pyridylphosphine
Oxydi-2,1-phenylenebis(diphenylphosphine)
Triphenylphosphine
Tris(1-naphthyl)phosphine
Tris(2,4,6-trimethoxyphenyl)phosphine
Tris(4-methoxyphenyl)phosphine
Tris(p-trifluoromethylphenyl)phosphine Example 33

Example 24 is substantially repeated in several runs using the following conditions. The reactions were carried out at various temperatures in different solvents as follows: 50° C. in acetonitrile, 80° C. in toluene, 120° C. and 160° C. in butyl benzoate. In all runs the amount of 2-ethylhexanoic acid used is 100 milligrams in combination with 500 ppm of para-benzoquinone and 10 milligrams of iridium complex catalyst except for runs in the presence of iridium(IV) oxide, in which case 2.5 milligrams of iridium(IV) oxide is used. Various iridium catalysts are summarized in Table 32.

TABLE 32

Catalyst (1,5-Cyclooctadiene)-hexafluoroacetylacetonato)iridium(I)
Bis(1,5-cyclooctadiene)diiridium(I) dichloride
Bis(1,5-cyclooctadiene)iridium(I) tetrafluoroborate
Ir(III) acetylacetonate
Ir(IV) oxide Example 34

A suitable reactor vessel equipped with appropriate inlets and stirring device is charged with 100 milligrams of neoheptanoic acid and 500 ppm of para-benzoquinone. The reactor is purged two to three times with nitrogen and a constant flow of nitrogen is maintained. To this mixture is added 900 milligrams of butyl benzoate with stirring and the mixture is heated slightly, if necessary, to dissolve neoheptanoic acid. To this solution is added 10 milligrams of platinum acetylacetonate with stirring and the entire mixture is heated to 140° C. At this time, acetylene is fed into the reactor at a steady stream maintaining the pressure of acetylene at 1.7 bars. The reaction mixture is stirred for an additional 4 hour period. At the end of this period, a sample of the reaction mixture is removed and analyzed by GC as described above.

Example 35

Example 34 is substantially repeated in several runs using the following conditions. The reaction temperature is maintained at either 120° C. or 160° C. Butyl benzoate is used as a solvent. The amount of neoheptanoic acid used is 100 milligrams in combination with 500 ppm of para-benzoquinone and 10 milligrams of platinum homogeneous catalyst. Various platinum catalysts that can be used in this Example are summarized in Table 33.

TABLE 33

| Catalyst | Temp. (° C.) |
|---|---|
| (1,5-Cyclooctadiene) dimethylplatinum(II) | 120 |
|  | 160 |
| Platinum acetylacetonate | 120 |
|  | 160 |
| Platinum(II) bromide | 120 |
|  | 160 |
| Platinum(II) chloride | 120 |
|  | 160 |
| Platinum(IV) chloride | 120 |
|  | 160 |
| Platinum(II) iodide | 120 |
|  | 160 |

Example 36

Example 34 is substantially repeated in several runs using the following conditions. Three different reaction temperatures are employed: 120° C., 140° C. and 160° C. Butyl benzoate is used as a solvent. The acid used is neopentanoic acid. The amount of neopentanoic acid used is 360 milligrams in combination with 500 ppm of para-benzoquinone and a desired amount of platinum homogeneous catalyst so as to maintain similar molar CA/metal ratio as in Example 34 or 35. Various ligands are also used with each of the platinum metal complex as summarized in Table 34.

TABLE 34

Catalyst/Ligand (1,5-Cyclooctadiene)dimethylplatinum(II)
(1,5-Cyclooctadiene)dimethylplatinum(II)/
4,5-Bis(diphenylphosphino)-9,9-dimethylxanthene
(1,5-Cyclooctadiene)dimethylplatinum(II)/
Oxydi-2,1-phenylenebis(diphenylphosphine)
(1,5-Cyclooctadiene)dimethyl-platinum(II)/
triphenylphosphine
Platinum acetylacetonate
Platinum acetylacetonate/
4,5-Bis(diphenylphosphino)-9,9-dimethylxanthene
Platinum acetylacetonate/
Oxydi-2,1-phenylenebis(diphenylphosphine)
Platinum acetylacetonate/triphenylphosphine
Platinum(II) iodide
Platinum(II) iodide/
4,5-Bis(diphenylphosphino)-9,9-dimethylxanthene
Platinum(II) iodide/
Oxydi-2,1-phenylenebis(diphenylphosphine)
Platinum(II) iodide/triphenylphosphine Example 37

Example 34 is substantially repeated in several runs using the following conditions. The reaction temperature is maintained at 140° C. for all of the runs. Butyl benzoate is used as a solvent. The acid used is pivalic acid (PA). The amount of pivalic acid used is 360 milligrams in combination with 500 ppm of para-benzoquinone. The necessary amount of platinum homogeneous catalyst is used to attain three different levels of molar PA/metal ratios of 385, 1155 and 3850. Various ligands are also used with each of the platinum metal complex as summarized in Table 35 with these varied molar PA/metal ratio.

TABLE 35

| Catalyst/Ligand | PA/metal ratio |
|---|---|
| (1,5-Cyclooctadiene)dimethylplatinum(II) | 385 |
|  | 1155 |
|  | 3850 |
| (1,5-Cyclooctadiene)dimethylplatinum(II)/ | 385 |
| 4,5-Bis(diphenylphosphino)-9,9-dimethylxanthene | 1155 |
|  | 3850 |
| (1,5-Cyclooctadiene)dimethylplatinum(II)/ | 385 |
| Oxydi-2,1-phenylenebis(diphenylphosphine) | 1155 |
|  | 3850 |
| (1,5-Cyclooctadiene)dimethyl-platinum(II)/ | 385 |
| triphenylphosphine | 1155 |
|  | 3850 |
| Platinum acetylacetonate | 385 |
|  | 1155 |
|  | 3850 |
| Platinum acetylacetonate/ | 385 |
| 4,5-Bis(diphenylphosphino)-9,9-dimethylxanthene | 1155 |
|  | 3850 |
| Platinum acetylacetonate/ | 385 |
| Oxydi-2,1-phenylenebis(diphenylphosphine) | 1155 |
|  | 3850 |
| Platinum acetylacetonate/triphenylphosphine | 385 |
|  | 1155 |
|  | 3850 |

Example 38

Example 34 is substantially repeated in several runs using the following conditions. Three different reaction temperatures are employed: 120° C., 140° C. and 160° C. Butyl benzoate is used as a solvent. The acid used is neodecanoic acid (NDA). The amount of neodecanoic acid used is 360 milligrams in combination with 500 ppm of para-benzoquinone and the appropriate amount of rhenium homogeneous catalyst is added to maintain similar molar NDA/metal ratios as in Example 34 or 35. Various ligands are also used with each of the rhenium metal complex as summarized in Table 36.

TABLE 36

| Catalyst/Ligand |
|---|
| Bromopentacarbonylrhenium(I) |
| Bromopentacarbonylrhenium(I)/ |
| 4,5-Bis(diphenylphosphino)-9,9-dimethylxanthene |
| Bromopentacarbonylrhenium(I)/ |
| Oxydi-2,1-phenylenebis(diphenylphosphine) |
| Bromopentacarbonylrhenium(I)/1,2-DPPB |
| Dirhenium decacarbonyl |
| Dirhenium decacarbonyl/ |
| 4,5-Bis(diphenylphosphino)-9,9-dimethylxanthene |
| Dirhenium decacarbonyl/ |
| Oxydi-2,1-phenylenebis(diphenylphosphine) |
| Dirhenium decacarbonyl/1,2-DPPB |
| Pentacarbonylchlororhenium(I) |
| Pentacarbonylchlororhenium(I)/ |
| 4,5-Bis(diphenylphosphino)-9,9-dimethylxanthene |
| Pentacarbonylchlororhenium(I)/ |
| Oxydi-2,1-phenylenebis(diphenylphosphine) |
| Pentacarbonylchlororhenium(I)/1,2-DPPB |

Example 39

Example 34 is substantially repeated in several runs using the following conditions. The reaction temperatures are maintained either at 50° C. (in acetonitrile as a solvent), 80° C. or 90° C. (in toluene as a solvent) or 120° C. (in butyl benzoate as a solvent). The acid used is dodecanoic acid. In all cases the amount of dodecanoic acid used is 100 milligrams in combination with 500 ppm of para-benzoquinone and 10 milligrams of rhodium homogeneous catalyst. Various rhodium catalysts used are summarized in Table 37.

TABLE 37

| Rhodium Catalysts |
|---|
| (Acetylacetonato)dicarbonylrhodium(I) |
| 1,1'-Bis(diisopropylphosphino)-ferrocene(cod)Rh-phosphotungstic acid |
| Bis(1,5-cyclooctadiene)-dirhodium(I)dichloride |
| Dichloro(pentamethylcyclopentadienyl)rhodium(III) dimer |
| Methoxy(cyclooctadiene)rhodium(I) dimer |

Example 40

Example 34 is substantially repeated in several runs using the following conditions. In all runs the reaction temperatures is maintained at 120° C. in butyl benzoate as a solvent. The acid used is octanoic acid. The amount of octanoic acid used is either 100 milligrams in combination with 500 ppm of para-benzoquinone or 360 milligrams in combination with 0.05 milligrams of para-benzoquinone. The catalyst used is rhodium(II) acetate dimer The amount of catalyst used is 10 milligrams with 100 milligrams of pentanoic acid or 2.5 milligrams of catalyst with 360 milligrams of pentanoic acid. Various ligands are used with the rhodium catalyst at ligand/metal ratio of one and are summarized in Table 38.

TABLE 38

| Ligand |
|---|
| 1,1'-Bis(diphenylphosphino)-ferrocene |
| 1,2-DPPB |
| 4,5-Bis(diphenylphosphino)-9,9-dimethylxanthene |
| Diphenyl-2-pyridylphosphine |
| Oxydi-2,1-phenylenebis-(diphenylphosphine) |
| Tris(p-trifluoromethylphenyl)phosphine |
| Triphenylphosphine |
| Tris(1-naphthyl)phosphine |
| Tris(2,4,6-trimethoxyphenyl)-phosphine |
| Tris(4-methoxyphenyl)-phosphine |

Example 41

Example 34 is substantially repeated in several runs using the following conditions. The reaction temperatures are maintained either at 50° C. (in acetonitrile as a solvent), 80° C. or 90° C. (in toluene as a solvent) or 120° C. (in butyl benzoate as a solvent). The acid used is neoheptanoic acid. In all cases the amount of neoheptanoic acid used is 100 milligrams in combination with 500 ppm of para-benzoquinone and 10 milligrams of ruthenium homogeneous catalyst. Various ruthenium catalysts and ligands used are summarized in Table 39.

TABLE 39

| Ruthenium Catalyst/Ligand |
|---|
| Bis(2-methylallyl)(1,5-cyclooctadiene)-ruthenium(II)/ 1,2-DPPB |
| Triruthenium dodecacarbonyl/Triphenylphosphine |
| Triruthenium dodecacarbonyl |
| Dichloro(p-cymene)tricyclohexylphosphine-ruthenium(II) |

TABLE 39-continued

Ruthenium Catalyst/Ligand

Tricarbonyldichlororuthenium(II) dimer
Triruthenium dodecacarbonyl/1,2-DPPB
Bis(2-methylallyl)(1,5-cyclooctadiene)ruthenium(II)/
Triphenylphosphine

Example 42

Example 34 is substantially repeated in several runs using the following conditions. The reaction temperatures are maintained either at 80° C. (in toluene as a solvent) or at 120° C. (in butyl benzoate as a solvent). The acid used in this example is neopentanoic acid. In all cases the amount of neopentanoic acid used is 230 milligrams in combination with 500 ppm of para-benzoquinone and 10 milligrams of palladium acetate as a catalyst. In each of these runs, various ligands are used with a constant molar ligand/metal ratio of 1.0 and are summarized in Table 40.

TABLE 40

Ligand 1,2-DPPB
Diphenyl-2-pyridylphosphine
Oxydi-2,1-phenylenebis(diphenylphosphine)
Triphenylphosphine
Tris(1-naphthyl)phosphine
Tris(2,4,6-trimethoxyphenyl)phosphine
Tris(4-methoxyphenyl)phosphine
Tris(p-trifluoromethylphenyl)phosphine

Example 43

Example 34 is substantially repeated in several runs using the following conditions. The reactions were carried out at various temperatures in different solvents as follows: 50° C. in acetonitrile, 80° C. in toluene, or 120° C. and 160° C. in butyl benzoate. The acid used is decanoic acid. In all runs the amount of decanoic acid used is 100 milligrams in combination with 500 ppm of para-benzoquinone and 10 milligrams of iridium complex catalyst except for runs in the presence of iridium(IV) oxide, in which case 2.5 milligrams of catalyst is used. Various iridium catalysts are summarized in Table 41.

TABLE 41

Catalyst (1,5-Cyclooctadiene)-hexafluoroacetylacetonato)iridium(I)
Bis(1,5-cyclooctadiene)diiridium(I) dichloride
Bis(1,5-cyclooctadiene)iridium(I) tetrafluoroborate
Ir(III) acetylacetonate
Ir(IV) oxide

Example 44

A suitable reactor vessel was equipped with appropriate inlets and stirring device and was charged with 65.15 grams of benzoic acid and 2 grams of methylhydroquinone. The reactor was purged two to three times with nitrogen and a constant flow of nitrogen was maintained. To this mixture, was added 134 grams of butyl benzoate with stirring and the mixture was heated slightly, if necessary, to dissolve benzoic acid. To this solution was added 0.47 grams of platinum acetylacetonate ($Pt(acac)_2$) with stirring and the entire mixture was heated to 160° C. At this time, acetylene was fed into the reactor at a steady stream and at a rate of 100 mL/min. The reaction mixture was stirred for an additional 4 hour period. At this time, a sample of the reaction mixture was removed and analyzed by GC as described above. From the GC analysis it was observed that 25.46 grams of vinyl benzoate was formed in the reaction mixture (32 percent yield). 24.69 grams of unreacted benzoic acid were recovered; Conversion of BA=62%; Selectivity to VB=52%; and the TON was 144.

Example 45

A suitable reactor vessel of the class shown in FIG. 1 was equipped with appropriate inlets and stirring device and was charged with 194.85 grams of 2-ethylhexanoic acid and 2 grams of methylhydroquinone. The reactor was purged two to three times with nitrogen and a constant flow of nitrogen was maintained. To this mixture was added 0.51 grams of platinum acetylacetonate ($Pt(acac)_2$) with stirring and the entire mixture was heated to 160° C. At this time, acetylene was fed into the reactor at a steady stream and at a rate of 100 mL/min. The reaction mixture was stirred for an additional 4 hour period. At this time, a sample of the reaction mixture was removed and analyzed by GC as described above. From the GC analysis it was observed that 16.19 grams of vinyl 2-ethylhexanoate was formed in the reaction mixture (7 percent yield). 150.3 grams of unreacted 2-ethylhexanoic acid were recovered; Conversion of 2-EHA =23%; Selectivity to V2EH =31%; and the TON was 73.

COMPARATIVE EXAMPLES

The following comparative examples illustrate the production of vinyl benzoate using conventional catalysts such as cadmium or zinc based catalysts.

Comparative Example 1

Example 1 was substantially repeated in several runs except for using cadmium acetate or cadmium acetylacetonate as the catalyst. The reactions were run at 150° C. or 180° C. in butyl benzoate, mineral oil or diethyleneglycoldibutylether as solvents. In all runs the amount of benzoic acid used was 100 milligrams in combination with 500 ppm of para-benzoquinone and 50 milligrams of the catalyst. Several of the ligands and additives were also used at a metal/ligand molar ratio of one. The tested ligands include triphenylphosphine and o-dipyridyl. The additives tested were the following: palladium(II) chloride, palladium(II) acetate, tetra-n-butylammonium chloride, aluminum chloride, aluminum acetylacetonate, cerium(III) chloride, lithium acetate, lithium chloride and ferric chloride. The results showed that the best performance of cadmium acetate or cadmium acetylacetonate was at 180° C. in butyl benzoate. A maximum TON of 0.9 with 30% selectivity to vinyl benzoate was obtained with cadmium acetylacetonate. No improvement was observed with any of the ligands and/or additives tested.

Comparative Example 2

Example 1 was substantially repeated in two runs except for using cadmium acetylacetonate as the catalyst with and without triphenylphosphine as a ligand. The reactions were run at 150° C. in butyl benzoate as a solvent. In both runs the amount of benzoic acid used was 100 milligrams in combination with 500 ppm of para-benzoquinone and 50 milligrams of the catalyst. The amount of triphenylphosphine was used at a metal/ligand molar ratio of one in a run with triphenylphosphine. The TON of ~0.2 was obtained.

Comparative Example 3

Example 1 was substantially repeated in several runs except for using zinc acetylacetonate as the catalyst. The reactions were run at 150° C. or 180° C. in butyl benzoate, mineral oil or diethyleneglycoldibutylether as solvents. The tested ligands include triphenylphosphine, 1,2-DPPB, tris(p-trifluoromethylphenyl)-phosphine and o-dipyridyl. The additives tested were the following: palladium(II) chloride, palladium(II) acetate, triruthenium dodecacarbonyl, ruthenium (III) chloride, cadmium acetylacetonate, tetra-n-butylammonium chloride, tetra-n-butylammonium acetate, aluminum chloride, aluminum acetylacetonate, cerium(III) chloride, sodium triflate, sodium tetrafluoroborate, lithium acetate, lithium chloride and ferric chloride. In all runs the amount of benzoic acid used was 100 milligrams in combination with 500 ppm of para-benzoquinone and 50 milligrams of the catalyst. Several of the ligands and additives were also used at a metal/ligand molar ratio of one. The results showed that the best performance of zinc catalyst system showed a TON of less than 0.5.

Comparative Example 4

Example 1 was substantially repeated except for using zinc acetylacetonate in combination with cadmium acetylacetonate as an additive. The reaction was run at 180° C. in butyl benzoate as the solvent. The amount of benzoic acid used was 100 milligrams in combination with 500 ppm of para-benzoquinone and 50 milligrams of the catalyst. The TON of ~0.51 was obtained. No improvement was observed with any of the ligands and/or additives tested.

Comparative Example 5

Example 1 was substantially repeated except for using zinc acetylacetonate as the catalyst. The reaction was run at 180° C. in butyl benzoate as the solvent. The amount of benzoic acid used was 100 milligrams in combination with 500 ppm of para-benzoquinone and 50 milligrams of the catalyst. The TON of ~0.45 was obtained.

While the invention has been described in connection with several embodiments, modifications of those embodiments within the spirit and scope of the present invention will be readily apparent to those of skill in the art. The invention is defined in the appended claims.

What is claimed is:

1. A homogeneous process for the selective formation of a vinyl ester from a carboxylic acid which comprises reacting the carboxylic acid with acetylene, optionally in a suitable organic solvent, at a suitable reaction temperature and suitable pressure in the presence of a Pt metal complex catalyst and optionally in the presence of a ligand, wherein Pt is provided in a molar ratio of carboxylic acid:Pt of about 200:1 to about 4000:1.

2. A homogeneous process for the selective formation of a vinyl ester from a carboxylic acid which comprises reacting the carboxylic acid with acetylene, optionally in a suitable organic solvent, at a suitable reaction temperature and suitable pressure for about 1-5 hours in the presence of a Pt metal complex catalyst and optionally in the presence of a ligand, wherein Pt is provided in a molar ratio of carboxylic acid:Pt of about 200:1 to about 4000:1.

3. A homogeneous process for the selective formation of a vinyl ester from a neo acid selected from neo acids according to Formula I:

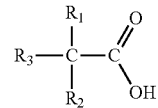

Formula I where each of $R_1$, $R_2$ and $R_3$ is an alkyl group having from 1 to 10 carbons and the total carbons in $R_1+R_2+R_3$ is from 3 to 30, which process comprises reacting the neo acid with acetylene, optionally in a suitable organic solvent, at a suitable reaction temperature and suitable pressure in the presence of a Pt metal complex catalyst and in the presence of a ligand, wherein Pt is provided in a molar ratio of carboxylic acid:Pt of about 200:1 to about 4000:1, and wherein the ligand is selected from the group consisting of triphenylphosphine, tris(4-methoxyphenyl)-phosphine, tris(p-trifluoromethylphenyl)-phosphine, tris(1-naphthyl)phosphine, tris(2,4,6-trimethoxyphenyl)phosphine, 1,2-diphenylphosphinobenzene (1,2-DPPB), o-bipyridyl, oxydi-(2,1-phenylene)bis(diphenylphosphine), (±)-2,2'-bis(diphenylphosphino)-1,1'-binaphthalene, 1,1'-bis(diphenylphosphino)-ferrocene, 1,2-bis(diphenylphosphino)benzene, diphenyl-2-pyridylphosphine and 4,5-bis(diphenylphosphino)-9,9-dimethylxanthene.

4. The process according to claim 1 wherein the ligand is present and selected from the group consisting of triphenylphosphine, tris(4-methoxyphenyl)-phosphine, tris(p-trifluoromethylphenyl)-phosphine, tris(1-naphthyl)phosphine, tris(2,4,6-trimethoxyphenyl)phosphine, 1,2-diphenylphosphinobenzene (1,2-DPPB), o-bipyridyl, oxydi-(2,1-phenylene)bis(diphenylphosphine), (±)-2,2'-bis(diphenylphosphino)-1,1'-binaphthalene, 1,1'-bis(diphenylphosphino)-ferrocene, 1,2-bis(diphenylphosphino)benzene, diphenyl-2-pyridylphosphine and 4,5-bis(diphenylphosphino)-9,9-dimethylxanthene.

5. The process of claim 1, wherein the reaction temperature ranges from about 40° C. to about 180° C.

6. The process according to claim 1, wherein the pressure of the reaction mixture is from about one atmosphere to two atmospheres absolute.

7. The process according to claim 1, wherein said ligand is present in a ligand:metal molar ratio of about 0.5:1 to about 1.5:1.

8. The process according to claim 1, wherein the carboxylic acid is selected from neo acids according to formula I:

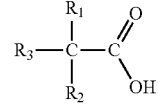

Formula I where each of $R_1$, $R_2$ and $R_3$ is an alkyl group having from 1 to 10 carbons and the total carbons in $R_1+R_2+R_3$ is from 3 to 30.

9. The process according to claim 8, wherein the neo acid is selected from the group consisting of: pivalic acid; neoheptanoic acid; neononanoic acid and neodecanoic acid.

10. The process according to claim 8, wherein the neo acid is neodecanoic acid.

11. The process according to claim 2, wherein the ligand is present and selected from the group consisting of triphenylphosphine, tris(4-methoxyphenyl)-phosphine, tris(p-trifluoromethylphenyl)-phosphine, tris(1-naphthyl)phosphine, tris(2,4,6-trimethoxyphenyl)phosphine, 1,2-diphenylphosphinobenzene (1,2-DPPB), o-bipyridyl, oxydi-(2,1-phenylene)bis(diphenylphosphine), (±)-2,2'-bis(diphenylphosphino)-1,1'-binaphthalene, 1,1'-bis(diphenylphosphino)ferrocene, 1,2-bis(diphenylphosphino)benzene, diphenyl-2-pyridylphosphine and 4,5-bis(diphenylphosphino)-9,9-dimethylxanthene.

12. The process of claim 2, wherein the reaction temperature ranges from about 40° C. to about 180° C.

13. The process according to claim 2, wherein the pressure of the reaction mixture is from about one atmosphere to two atmospheres absolute.

14. The process according to claim 2, wherein said ligand is present in a ligand:metal molar ratio of about 0.5:1 to about 1.5:1.

15. The process according to claim 2, wherein the carboxylic acid is selected from neo acids according to Formula I:

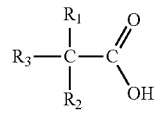
Formula I where each of $R_1$, $R_2$ and $R_3$ is an alkyl group having from 1 to 10 carbons and the total carbons in $R_1+R_2+R_3$ is from 3 to 30.

16. The process according to claim 15, wherein the neo acid is selected from the group consisting of: pivalic acid; neoheptanoic acid; neononanoic acid and neodecanoic acid.

17. The process according to claim 15, wherein the neo acid is neodecanoic acid.

18. The process according to claim 3, wherein the neo acid is selected from the group consisting of: pivalic acid; neoheptanoic acid; neononanoic acid and neodecanoic acid.

* * * * *